United States Patent [19]

Buckle

[11] Patent Number: 4,713,486

[45] Date of Patent: Dec. 15, 1987

[54] NOVEL COMPOUNDS

[75] Inventor: Derek R. Buckle, Redhill, England

[73] Assignee: Beecham Group p.l.c., Brentford, England

[21] Appl. No.: 789,571

[22] Filed: Oct. 21, 1985

[30] Foreign Application Priority Data

| Nov. 11, 1982 | [GB] | United Kingdom | 8232229 |
| Nov. 12, 1982 | [GB] | United Kingdom | 8232430 |
| Nov. 23, 1982 | [GB] | United Kingdom | 8233341 |
| Jun. 10, 1983 | [GB] | United Kingdom | 8315963 |
| Jun. 21, 1983 | [GB] | United Kingdom | 8316809 |
| Jul. 6, 1983 | [GB] | United Kingdom | 8318263 |
| Jul. 30, 1983 | [GB] | United Kingdom | 8320592 |

[51] Int. Cl.$^4$ .......................................... C07C 63/64
[52] U.S. Cl. ................................... 562/495; 562/471; 560/61; 560/104; 514/570; 514/571
[58] Field of Search .................. 562/495, 471; 560/61, 560/104; 514/570, 571

[56] References Cited

U.S. PATENT DOCUMENTS 4,362,891 12/1982 Guerralo et al. .................... 562/495

Primary Examiner—Paul J. Killos
Attorney, Agent, or Firm—Hopgood, Calimafde, Kalil, Blaustein & Judlowe

[57] ABSTRACT

A compound of formula (I):

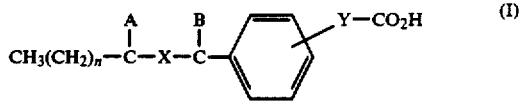

or a salt, ester or amide thereof, in which

Y is a group $-O(CH_2)_m-$, $-(CH_2)_m-$ or $-CH=CH-$ where m is an integer of from 1 to 5 n is an integer of from 4 to 14

X represents a double or triple bond, and each of A and B represents hydrogen when X is a double bond, or both A and B are absent when X is a triple bond, is useful in the treatment of allergic diseases.

13 Claims, No Drawings

NOVEL COMPOUNDS

This invention relates to novel arachidonic acid analogues, pharmaceutical compositions containing them and processes for their preparation.

It is known that certain arachidonic acid metabolities can produce harmful effects in man. For example, some prostaglandins and thromboxanes, produced via cyclooxygenation of arachidonic acid, can contribute to inflammation in such diseases as rheumatoid arthritis, and that products produced via lipoxygenation of arachidonic acid, such as the leukotrienes, are implicated in the production of the pathology of asthma and other allergic diseases.

We have now discovered a class of compounds which can inhibit arachidonic acid metabolism by one or both of these metabolic pathways and are thus of value in the prophylaxis and treatment of diseases whose symptoms are controlled by these mediators.

According to the present invention there is provided a compound of formula (I):

or a salt, ester or amide thereof,
in which
   Y is a group $-O(CH_2)_m-$, $-(CH_2)_m-$ or $-CH=CH-$ where m is an integer of from 1 to 5 n is an integer of from 4 to 14
   X represents a double or triple bond, and each of A and B represents hydrogen when X is a double bond, or both A and B are absent when X is a triple bond.

When X is a double bond, the hydrocarbon chain containing X may have the (E) or (Z) absolute configuration, preferably (Z).

Similarly, when Y is $-CH=CH-$, the $-Y-CO_2H$ group may have the (E) or (Z) absolute configuration, preferably (E).

The compounds of this invention can exist, therefore, in up to four geometric isomeric forms, and the invention encompasses all geometric isomers of the compounds of formula (I) whether as individual isomers or admixed with each other in any proportion.

The substituents on the aromatic ring may be in the 1,2; 1,3; or 1,4 positions, preferably in the 1,2 position.

Salts, esters or amides of compounds of formula (I) need not be pharmaceutically acceptable, since they can be used as intermediates to prepare other pharmaceutically acceptable compounds of the invention.

Examples of pharmaceutically acceptable esters of the compounds of formula (I) are those wherein the carboxyl group is modified to a group $-CO_2R^1$, wherein $R^1$ is a $C_{1-6}$ alkyl group, preferably methyl or ethyl.

Examples of pharmaceutically acceptable amides are those wherein the carboxyl group is modified to a group $-CONR^2R^3$, wherein $R^2$ and $R^3$ are each hydrogen or $C_{1-6}$ alkyl.

Examples of pharmaceutically acceptable salts include alkali metal and alkaline earth metal salts, such as sodium, potassium and magnesium salts,; and salts with ammonia, organic bases and amino compounds.

Preferably, n is an integer of from 4 to 12, particularly 8 to 12.

Preferably, m is 2, 3 or 4.

Examples of sub-groups within the general formula (I) are compounds of formulae (IA), (IB), (IC), (ID) and (IE), or salts, esters or amides thereof:

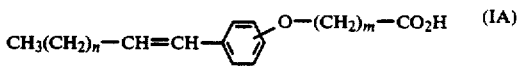

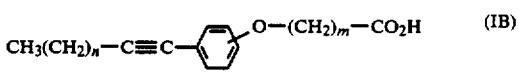

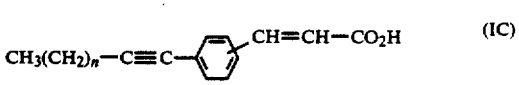

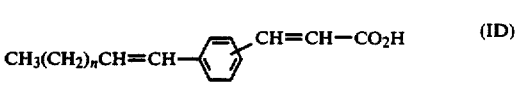

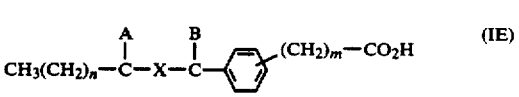

in which m, n, X, A and B are as defined with reference to formula (I),

According to a further aspect of the invention there is provided a process for preparing a compound of the invention which comprises treating a compound of formula (II),

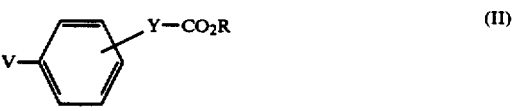

in which Y is as defined with reference to formula (I), V represents

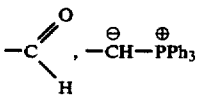

or halogen, preferably bromine or iodine, and R is hydrogen or, preferably, an ester forming group, with a compound of formula (III),

in which W is

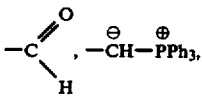

$-CH=CH_2$ or $-C≡CH$, and, optionally thereafter reducing the carbon-carbon triple bond, when present in the resultant product, to a carbon-carbon double bond, and/or optionally converting the resultant product, when R is an ester-forming group, to the corresponding acid or amide, with the provisos that
(i) when V is

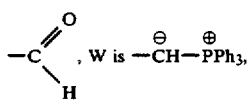

(ii) when V is

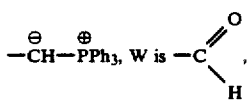

and (iii) when V is halogen, W is —CH=CH₂ or —C≡CH

When V is halogen, preferably bromine or iodine and W is —CH=CH₂ or C≡CH, the reaction is preferably carried out by refluxing the reactants in the presence of a palladium (II) salt/triarylphosphine catalyst in a tertiary amine, such as triethylamine, as a diluent and proton sink. A preferred catalyst is palladium acetate/triphenylphosphine, Pd(OAc)₂[Ph₃P]₂.

The resultant compound of the invention may be separated from the reaction mixture by chromatography of the filtered and evaporated reaction mixture.

When W is —CH=CH₂, the process is stereospecific to the extent that the CH₃(CH₂)ₙ—W— chain in the resultant product has the (E) configuration.

When V or W is

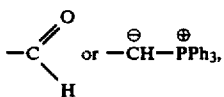

the reaction is preferably carried out in a suitable solvent, preferably dimethylsulphoxide or tetrahydrofuran, at ambient temperature and the product purified chromatographically. The reaction will generally produce a mixture of geometrical isomers which can be separated in conventional manner, such as by chromatography, for example an argentated silica gel.

When the resultant compound of the invention formed by reacting compounds of formula (II) and (III) includes a carbon-carbon triple bond, as will occur when W is —C≡CH, a further compound of the invention may be formed by reducing the triple bond to a double bond. This reduction may be carried out by conventional literature procedures, preferably by hydrogenation in the presence of a Lindlar catalyst, or other poisoned catalyst such as palladium on barium sulphate. This reduction tends to be stereospecific to the extent that the CH₃(CH₂)ₙ—W— chain in the resultant compound of the invention has the (Z) configuration.

When R is an ester forming group in the compound of formula (II), the resultant compound of the invention will also contain R, and this may be quantitatively hydrolysed with base, for example lithium hydroxide in aqueous tetrahydrofuran, to give an acid of formula (I). The ester may be converted to a corresponding amide, as required, by treatment with an alcoholic amine or by prior conversion, via the acid, to its acyl chloride by treatment with oxalyl chloride followed by reaction with the appropriate amine in an inert solvent.

The intermediate compounds of formula (II) may be prepared in a number of ways, as described hereinafter.

Compounds of formula (II) in which Y is —O(CH₂)ₘ— and V is

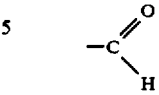

may be prepared by treating an hydroxy benzaldehyde with a bromo-alkanoate ester of formula (IIA)

$$Br-(CH_2)_m-CO_2R \quad (IIA)$$

wherein m is as defined in formula (I) and R is an ester forming group, according to the general method disclosed in British Patent Specification No. 1350883.

Compounds of formula (II) in which Y is —O(CH₂)ₘ— and V is

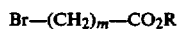

may be prepared by treating a compound of formula (IIB).

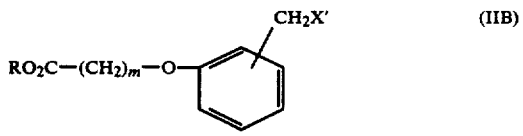

in which m is as defined in formula (I), R is an ester forming group, and X' is halogen, preferably bromine, with triphenylphosphine to form the phosphonium salt, followed by proton abstraction with a strong base such as n-butyl lithium.

Compounds of formula (IIB) may themselves be prepared by reducing a compound of formula (II) in which Y is —O(CH₂)ₘ— and V is

to the corresponding alcohol, and subsequently treating the alcohol with a halogenating agent. The reduction is conveniently carried out by borohydride reduction, and a preferred halogenating agent is carbon tetrabromide triphenyl phosphine.

Compounds of formula (II) in which Y is —(CH₂)ₘ—, V is

and R is an alkyl group, may be prepared by treating a compound of formula (IIC).

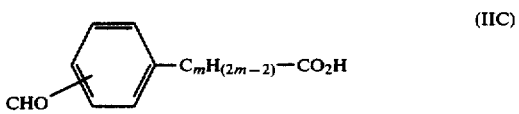

wherein the —C_mH_{(2m-2)}— group contains a carbon-carbon double bond, with an alkyl halide, preferably with potassium carbonate in dimethylformamide, and subsequently reducing the carbon-carbon double bond of the resultant ester.

The reduction is suitably carried out by first treating the ester with ethylene glycol to protect the formyl group, then reducing the carbon-carbon double bond, preferably by hydrogenation in the presence of a palladium catalyst, and finally de-protecting the formyl group by acidolysis.

Alternatively, the compounds of formula (II) in which Y is —(CH_2)_m—, V is

and R is alkyl may be prepared by esterification of the parent carboxylic acids, in accordance with known procedures. The parent carboxylic acids may themselves be prepared according to the methods disclosed in U.S. Pat. Nos. 3,969,373 and 3,860,639.

Compounds of formula (II) in which Y is —CH=CH—, V is

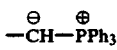

and R is an ester forming group may be prepared by reacting a compound of formula (IID).

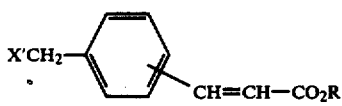
(IID)

wherein X' is halogen, preferably bromine, with triphenylphosphine, and subsequently treating the resulting compound of formula (IIE).

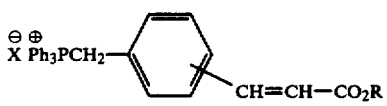
(IIE)

with sodium methylsulphinylmethylide in dimethylsulphoxide.

Compounds of formula (IID) may themselves be prepared in an analogous manner to those of formula (IIB).

Compounds of formula (II) in which V is halogen and Y and R are as defined in formula (II) are either known compounds or can be prepared from known compounds by known methods. Also, compounds of formula (II) in which Y is —CH=CH— and V is

are known compounds or can be prepared from known compounds by known methods.

The intermediate compounds of formula (III) in which W is

—CH=CH_2 or —C≡CH are either known compounds or can be prepared from known compounds by known methods.

The compounds of formula (III) in which W is

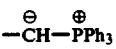

may be prepared by reacting the corresponding phosphonium bromide with sodium methylsulphinylmethylide, according to the method described in J. Org. Chem., 28, 1128, 1963 (Greinwald et al), or by reaction with butyl lithium in tetrahydrofuran.

Compounds of the invention may also be prepared by alternative processes, described as follows.

Esters of compounds of formula (I) in which Y is —(CH_2)_m— and X is double bond or triple bond may be prepared by treating a phenol of formula (IV).

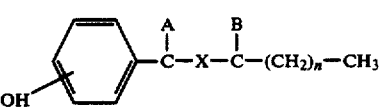
(IV)

wherein n, X, A and B are as defined in formula (I), with a compound of formula (V).

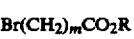
Br(CH_2)_mCO_2R    (V)

wherein m is as defined in formula (I) and R is an ester forming group.

The reaction is preferably carried out in a basic medium, such as potassium carbonate in butanone, and, when X is a double bond, the stereochemistry of the final product of formula (I) will be the same as that of the phenol of formula (IV). Therefore, this process can be used as a stereospecific synthesis of compounds of formula (I).

Compounds of formula (IV) in which X is a double bond can be prepared by treating an hydroxy benzaldehyde with a compound of formula (III), in which W is

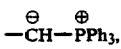

preferably in a solvent such as dimethylsulphoxide or tetrahydrofuran at ambient temperature. Compounds of formula (IV) in which X is a triple bond may be prepared by treating an alkyne of formula (IVA).

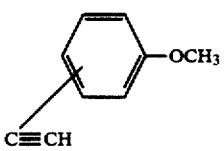
(IVA)

with an alkyl iodide of formula (IVB).

 (IVB)

to yield a compound of formula (IVC)

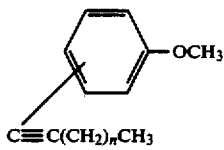 (IVC)

followed by demethylation of the compound of formula (IVC) by using conventional dealkylation methods.

Compounds of formula (I) or esters thereof in which Y is —CH=CH— and X is a triple bond may be prepared by treating a compound of formula (VI).

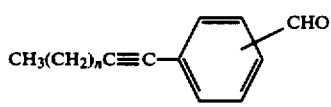 (VI)

in which n is as defined in formula (I) with a compound of formula (VII).

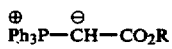 (VII)

in which R is an ester forming group as defined in formula (II). The reaction is preferably carried out by refluxing the reactants in toluene as a diluent.

The compounds of formula (VI) may themselves be prepared by treating a compound of formula (VIII).

 (VIII)

in which $X^2$ is bromine or iodine, preferably bromine, with a compound of formula (IX).

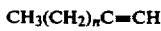 (IX)

in which n is as defined in formula (I).

The reaction is preferably carried out by refluxing the reactants in the presence of a palladium (II) salt/triarylphosphine catalyst, as described hereinbefore.

Compounds of formulae (V), (VII), (VIII) and (IX) are either known compounds or can be prepared from known compounds by known methods.

Esters of compounds of formula (I) in which Y is —O—$(CH_2)_m$— or —$(CH_2)_m$— and X is a triple bond may be prepared by brominating an ester of a compound of formula (I) in which Y is —O—$(CH_2)_m$— or —$(CH_2)_m$— and X is a double bond, and dehydrobrominating the resultant intermediate in which the

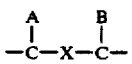

moiety in formula (I) is replaced by

—CHBr—CHBr—.

The dehydrobromination is preferably carried out with a strong base, such as potassium t-butoxide in dimethyl sulphoxide.

The compounds of formula (I) are active therapeutically, and, accordingly, this invention also provides a pharmaceutical composition comprising a compound of formula (I) as defined above, or a pharmaceutically acceptable salt, ester or amide thereof, and a pharmaceutically acceptable carrier.

A compound of formula (I), or salt, ester or amide thereof which is active when given by the oral route, may be compounded in the form of syrups, tablets, capsules, pills and the like. Preferably, the composition is in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

Compositions of this invention may also suitably be presented for administrationn to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A compound of general formula (I) or salt, ester or amide thereof may also be presented as an ointment, cream, lotion, gel, aerosol, or skin paint for topical application.

It is preferred that the compounds of this invention are administered by inhalation.

By way of example, in any of the preceding formulations a suitable dosage unit might contain 0.01 to 500 mgs of active ingredient, more suitably 1 to 500 mgs via the oral route, 0.01 to 10 mgs via inhalation. The effective dose of compound depends on the particular compound employed, the condition of the patient and on the frequency and route of administration, but in general is in the range of from 0.001 mg/kg/day to 100 mg/kg/day inclusive of the patient's body weight.

As in common practice, the compositions will usually be accompanied by written or printed directions for use in the medical treatment concerned, in this case as an anti-allergic agent for the prophylaxis and treatment of, for example, asthma, hay fever, rhinitis or allergic eczema.

The invention also provides a method for treating allergic diseases in human and non-human animals, which comprises administering to the sufferer an effective non-toxic amount of a compound of formula (I) or a pharmaceutically acceptable salt, ester or amide thereof.

The following Examples illustrate the preparation of compounds of this invention.

EXAMPLE 1

Methyl 4-bromocinnamate

Anhydrous potassium carbonate (20.7 g, 0.15 mmole) was added to a solution of 4-bromocinnamic acid (22.7 g, 0.1 mmole) in dry N,N-dimethylformamide (150 ml) and the mixture was stirred for 30 minutes. Methyl iodide (21.3 g, 9.4 ml, 0.15 mmole) was then added and the total mixture stirred for a further 24 hours at room temperature before the solvent was evaporated in vacuo. Water was added to the residue and the product extracted into ether. The ethereal extracts were washed with saturated aqueous sodium bicarbonate solution, the brine and dried ($MgSO_4$). Evaporation afforded 22.73 g (94%) of the ester as a white solid of mp (methanol) 82°–86° C. (lit mp 80° C., Dictionary of Organic Compounds), $\nu_{max}$ (mull), 1718, 1640, 1595, 1495 $cm^{-1}$. $\delta(CDCl_3)$ 3.80 (3H, s, ester $CH_3$), 6.37 (1H, d, J 13 Hz, =$CHCO_2$), 7.42 (4H, m, arom), 7.62 (1H, d, J 13 Hz, ArCH=).

The NMR shows evidence of some 20% of the (Z)-isomer.

EXAMPLE 2

Methyl 3-bromocinnamate

Reaction of 3-bromocinnamic acid (22.72 g) with methyl iodide (21.3 g) as described in Example 1 gave the title ester (19.5 g, 81%) as a white solid mp (methanol) 62°–65° C.

$\nu_{max}$ (mull) 2920, 1725, 1640, 1560, 1465, 1315, 1200, 1170, 985, 865, and 790 $cm^{-1}$, $\delta(CDCl_3)$ 3.82 (3H, s, ester $CH_3$), 6.36 (1H, d, J=16 Hz, C=$CHCO_2$), 7.03–7.7 (4H, m, aromatic H), and 7.56 (1H, d, J=16 Hz, ArCH=).

EXAMPLE 3

Methyl 2-bromocinnamate

Esterification of 2-bromocinnamic acid (10.0 g) with methyl iodide (9.4 g) as described in Example 1 gave the title compound as an oil which was purified by chromatography on silica eluting with chloroform in quantitative yield. $\nu_{max}$ (film) 1725, 1640, 1470, 1440 $cm^{-1}$, $\delta(CDCl_3)$ 3.79 (3H, s, $CH_3$), 6.30 (1H, d, J 16 Hz, C=$CHCO_2$), 7.19 (2H, complex m), 7.50 (2H, complex m), 7.97 (1H, d, J 16 Hz, ArCH=C).

EXAMPLE 4

Methyl 4-(1-tridecynyl)cinnamate

To a deaerated solution of methyl 4-bromocinnamate (9.64 g, 40 mmole) in dry triethylamine (120 ml) was added triphenylphosphine (308 mg) followed by 1-tridecyne (8.00 g, 45 mmole) and palladium (II) acetate (92 mg) under nitrogen. The mixture was heated to reflux for 24 hours, the reaction being followed by hplc. After this time the mixture was cooled and the precipitated triethylamine hydrobromide was filtered off and washed with a little triethylamine. The filtrate was evaporated to a red solid which was chromatographed on 220 g of silica eluting with petroleum ether [bp 60–80]-dichloromethane (3:2) to give 6.26 g (47%) of title compound as a pale yellow solid of mp (MeOH) 57°–59° C., $\nu_{max}$ (mull) 1710, 1630, 1600, 1315, 1170, 1000, 830 $cm^{-1}$, $\delta(CDCl_3)$. 0.85 (3H, distorted t, terminal $CH_3$), 1.28 (18H, m, alkylene chain), 2.38 (2H, t, J 6.5 Hz, C≡C—$CH_2$), 3.78 (3H, s, ester $CH_3$), 6.37 (1H, d, J 16 Hz, =$CHCO_2$), 7.42 (4H, near s, arom), 7.63 (1H, d, J 16 Hz, ArCH=)

Found C, 80.85 H, 9.73 $C_{23}H_{32}O_2$ requires C, 81.13 H, 9.47%.

Examples 5 to 8 (Table 1) were prepared in a similar manner to that outlined in Example 4.

TABLE 1

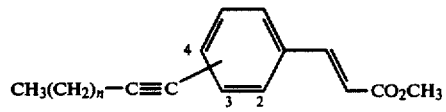

$CH_3(CH_2)_n$—C≡C— [aryl positions 4,3,2] —$CO_2CH_3$

| Example No. | Position of side chain n | attachment | m.p. °C. | Recrystalisation solvent | Yield % | Formula | Analysis (calcd/Found) C | H |
|---|---|---|---|---|---|---|---|---|
| 5 | 11 | 4 | 52–54 | $CH_3OH$ | 54 | $C_{24}H_{34}O_2$ | 81.31 / 81.33 | 9.67 / 9.56 |
| 6 | 7 | 4 | 43 | $CH_3OH$ | 28 | $C_{20}H_{26}O_2$ | 80.50 / 80.73 | 8.70 / 8.76 |
| 7 | 10 | 2 | oil | — | 81 | $C_{23}H_{32}O_2$ | 81.13 / 80.57 | 9.47 / 9.54 |
| 8 | 10 | 3 | 25–26.5 | $CH_3OH$ | 42 | $C_{23}H_{32}O_2$ | 81.13 / 81.30 | 9.47 / 9.40 |

EXAMPLE 9

4-(1-Tridecynyl)cinnamic acid

To a solution of methyl 4-(1-tridecynyl)cinnamate (680 mg, 2 mmole) in tetrahydrofuran (25 ml) was added a solution of lithium hydroxide monohydrate (0.84 g) in water (25 ml) and the mixture was stirred overnight at room temperature. The cloudy mixture was acidified with dilute hydrochloric acid and then extracted with ether. The ethereal extracts were washed with brine, dried (MgSO$_4$) and evaporated to a white crystalline solid. Yield 0.650 g (100%). Recrystallisation from methanol afforded material of mp 156°–157° C., $\nu_{max}$ mull, 2650 (broad), 1710, 1685, 1630 cm$^{-1}$, δ(DMSO), 0.85 (3H, distorted t, terminal CH$_3$), 1.25 (18H, m, alkylene chain), ca 2.43 (2H, m, C≡C—CH$_2$), 6.50 (1H, d, J 15.8 Hz, =CHCO$_2$), 7.51 (4H, ABq, J 8.4 Hz, Δ$\nu$22.4 Hz, arom), 7.57 (1H, d, J 15.8 Hz, ArCH=), 12.5 (1H, broad, exchangeable, CO$_2$H).

Found C, 80.91; H, 9.19; C$_{22}$H$_{30}$O$_2$ requires C, 80.94; H, 9.26%.

Examples 10 to 13 (Table 2) were prepared in a similar manner to that outlined in Example 9.

was cooled in an ice-water bath and a solution of n-dodecyl triphenylphosphonium bromide (11.30 g, 22 mmole) in dry dimethylsulphoxide (24 ml) was added. The mixture was stirred for 10 mins at room temperature and a solution of methyl 4-formylcinnamate (3.80 g, 22 mmole) in dry dimethylsulphoxide (10 ml) was added such that the reaction did not become warm. The mixture was stirred overnight at room temperature and poured into 10% aqueous sodium chloride (400 ml) and extracted with hexane. The hexane extracts were washed with water and then brine and dried (MgSO$_4$). Evaporation gave crude material which was chromatographed on 200 g of silica gel eluting with petroleum ether [bp 60–80]-dichloromethane (3:2), the fractions being monitored by hplc.

TABLE 2

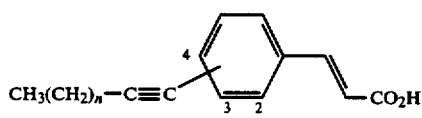

| Example No. | Position of side chain | | Recrystalisation | | Yield % | Formula | Analysis (calcd/Found) | |
|---|---|---|---|---|---|---|---|---|
| | n | attachment | m.p. °C. | solvent | | | C | H |
| 10 | 11 | 4 | 152–154 | CH$_3$OH | 100 | C$_{23}$H$_{32}$O$_2$ | 81.13 | 9.47 |
| | | | | | | | 81.43 | 9.28 |
| 11 | 7 | 4 | 150–155 | C$_2$H$_5$OH | 57 | C$_{19}$H$_{24}$O$_2$ | 80.24 | 8.51 |
| | | | | | | | 80.40 | 8.62 |
| 12 | 10 | 2 | 69–72 | CH$_3$OH | 100 | C$_{22}$H$_{30}$O$_2$ | 80.94 | 9.26 |
| | | | | | | | 80.87 | 9.52 |
| 13 | 10 | 3 | 105–106 | CH$_3$OH | 98 | C$_{22}$H$_{30}$O$_2$ | 80.94 | 9.26 |
| | | | | | | | 80.83 | 9.41 |

EXAMPLE 14

Methyl 4-formylcinnamate

A mixture of 4-formylcinnamic acid (7.04 g, 40 mmole), anhydrous potassium carbonate (16.5 g, 120 mmole) and methyl iodide (8.5 g, 60 mmole) in dry N,N-dimethylformamide (50 ml) was stirred overnight at room temperature and the solvent evaporated in vacuo. The product was partitioned between ether and water and the organic phase washed with brine and dried (MgSO$_4$). Evaporation gave 7.32 g (97%) of the title ester of mp (aqueous methanol) 83°–85° C., $\nu$max (mull) 1723, 1683, 1635 cm$^{-1}$, δ(CDCl$_3$) 3.83 (3H, s, CH$_3$), 6.52 (1H, d, J15 Hz, C=CHCO$_2$), 7.75 (1H, d, J 15 Hz, ArCH=C), 7.79 (4H, ABq, J 6 Hz, Δ$\nu$16.5 Hz, arom), 10.08 (1H, s, CHO).

Found: C, 69.70; H, 5.12; C$_{11}$H$_{10}$O$_3$ Requires: C, 69.46; H, 5.30%.

EXAMPLES 15 AND 16

Methyl 4-[(Z)-1-tridecenyl]cinnamate (Example 15) and Methyl 4-[(E)-1-tridecenyl]cinnamate (Example 16)

Sodium hydride (1.06 g, 22 mmole of a 50% dispersion in mineral oil) was weighed into a dry 100 ml round bottom three necked flask and washed by decantation with petroleum ether. The air was replaced by nitrogen, dry dimethylsulphoxide (12 ml) was added and the mixture was stirred at 75°–80° C. for 45 minutes until evolution of hydrogen ceased. The resulting solution The first fraction gave 1.122 g of pure (Z) isomer (Example 15) of mp (isopropanol) 60°–62° C., $\nu$max (mull) 1725, 1640, 1325, 1315, 1215, 1170 cm$^{-1}$. δ(CDCl$_3$) 0.84 (3H, distorted t, terminal CH$_3$), 1.30 (18H, m, alkylene chain), 2.30 (2H, m, allylic CH$_2$), 3.80 (3H, s, ester CH$_3$), 5.68 (1H, d.t, J$_d$ 12 Hz, J$_t$ 7.2 Hz, C=CH—alkyl), 6.37 (1H, split d, J 12 Hz, ArHC=C—alkyl), 6.38 (1H, d, J 15.5 Hz, C=CHCO$_2$), 7.36 (4H, ABq, J 8 Hz, Δ$\nu$18 Hz, arom), 7.67 (1H, d, J 15.5 Hz, ArCH=C—CO$_2$).

Found: C, 80.67; H, 10.21; C$_{23}$H$_{34}$O$_2$ Requires: C, 80.65; H, 10.01%

Further elution gave 1.900 g of a 1:1 mixture of the (E) and (Z) isomers followed by 0.234 g of >90% pure (E) isomer (Example 16) of mp (carbon tetrachloride, isopropanol) 62° C., $\nu$max (mull) 1715, 1640, 1603, 1180 cm$-1$; (CDCl$_3$) 0.85 (3H, distorted t, CH$_3$CH$_2$), 1.30 (18H, m, alkylene chain), 2.18 (2H, m, allylic CH$_2$), 3.78 (3H, s, ester CH$_3$), 6.32 (2H, m, vinylic protons), 6.39 (1H, d, J 15 Hz, C=CH—CO$_2$), 7.39 (4H, AB quartet, J 7.5 Hz, Δ$\nu$12 Hz, aromatics), 7.67 (1H, d, J 15 Hz, ArCH=C—CO$_2$) λmax (isooctane) 311 (33,700) nm, Found: C, 80.72; H, 10.39; C$_{23}$H$_{34}$O$_2$ Requires: C, 80.65; H, 10.01%.

Total yield=3.26 g (48%) of (E) and (Z) isomers in the ratio 35:65.

Examples 17 to 20 (Table 3) were prepared in a similar manner to that outlined in Examples 15 and 16.

TABLE 3

CH₃(CH₂)ₙ—*—[phenyl]—CH=CH—CO₂CH₃

| Example No. | n | Stereochemistry of the asterisked double bond | m.p. °C. | Recrystalisation solvent | Yield % | Formula | Analysis (calcd/Found) C | H |
|---|---|---|---|---|---|---|---|---|
| 17 | 8 | Z | 49–50 | CH₃OH | 19 | C₂₁H₃₀O₂ | 80.21 | 9.62 |
|    |   |   |       |        |    |          | 80.27 | 9.81 |
| 18 | 8 | E | 53–55 | CH₃OH |    | C₂₁H₃₀O₂ | 80.21 | 9.62 |
|    |   |   |       |        |    |          | 80.51 | 9.35 |
| 19 | 12 | Z | 63–64 | CH₃OH | 50 | C₂₅H₃₈O₂ | 81.00 | 10.33 |
|    |    |   |       |        |    |          | 80.88 | 10.04 |
| 20 | 12 | E | 65–66 | CH₃OH |    | C₂₅H₃₈O₂ | 81.00 | 10.33 |
|    |    |   |       |        |    |          | 81.09 | 10.47 |

EXAMPLE 21

Methyl 4-[(Z)-1-tridecenyl]cinnamate

A solution of methyl 4-(1-tridecynyl)cinnamate (1.020 g, 3 mmole from Example 4) in pyridine (20 ml) was hydrogenated in the presence of 5% palladium on barium sulphate (24 mg) until 1 equivalent of hydrogen was absorbed. After removal of the catalyst by filtration the solvent was removed to give the alkene as a pale yellow solid. Recrystallization from methanol gave 885 mg (87%) of pure (Z) alkene of mp 60°–62° C. indentical with that of Example 15.

EXAMPLE 22

Methyl 2-[(Z)-1-tridecenyl]cinnamate

Hydrogenation of methyl 2-(1-tridecynyl)cinnamate (1.02 g, 3 mmole, from Example 7) as described in Example 21 gave 0.915 g (89%) of the (Z) alkene as a colourless oil after chromatography with 1:1 dichloromethane-petrol [bp 60–80] on silica. It had $\nu$max (film) 1720, 1630, 1315, 1170 cm$^{-1}$, δ(CDCl₃) 0.84 (3H, t, terminal CH₃), 1.23 (18H, m, alkylene chain), 2.00 (2H, m, allylic CH₂), 3.78 (3H, s, ester CH₃), 5.77 (1H, d, t, $J_d$ 12 Hz, $J_t$ 7.5 Hz, C=CH—R), 6.21 (1H, d, J 16 Hz, C=CHCO₂), 6.49 (1H, d, J 12 Hz, ArCH=C—R), 7.18 (3H, m, arom), 7.52 (1H, m, arom), 7.87 (1H, d, J 16 Hz, ArCH=C—CO₂).

M⁺ found 342.2561, calculated for C₂₃H₃₄O₂, 342.2559.

EXAMPLE 23

Methyl 3-[(Z)-1-Tridecenyl]cinnamate

Hydrogenation of methyl 3-[1-tridecynyl]cinnamate (1.02 g 3 mmole) from example 18 as described in example 21 gave 0.553 g (54%) of the (Z) alkene as a colourless oil after chromatography with 1:2 dichloromethane-petrol (b.p. 60–80) on silica containing 10% silver nitrate. $\nu$max (film) 2910, 1720, 1640, 1435, 1315, 1260, 1170, 800 cm$^{-1}$, δ(CDCl₃) 8.5 (3H, t, J=6.7 Hz terminal CH₃) 1.26 (18H, m, alkyl chain), 2.25 (2H, m, allylic CH₂), 3.80 (3H, s, ester CH₃), 5.7 (1H, d, t, $J_d$=12 Hz, $J_t$=7.5 Hz, C=CH—R), 6.4 (1H, d, J=12 Hz, ArCH=C—R), 6.42 (1H, d, J=15 Hz, C=CH—CO₂) 7.35 (4H, m, arom), 7.7 (1H, d, J=15 Hz, Ar—CH=C—CO₂).

M± found 342.2554, calculated for C₂₃H₃₄O₂ 342.2559.

EXAMPLE 24

4-[(E)-1-Tridecenyl]cinnamic acid

To a solution of methyl 4-[(E)-1-tridecenyl]cinnamate (342 mg, 1 mmole from Example 16 in 50% aqueous tetrahydrofuran (25 ml) was added lithium hydroxide monohydrate (420 mg, 10 equivalents) and the mixture was stirred at room temperature overnight. The cloudy mixture was acidified with dilute hydrochloric acid and extracted with ether. The extracts were washed with brine, dried (magnesium sulphate) and evaporated to a white crystalline solid. Yield 330 mg (100%). Recrystallisation from methanol afforded material of mp 107° C., $\nu$max (mull) 2600 (broad), 1710, 1680, 1625, 1425, 1308, 1285 cm$^{-1}$; δ(DMSO-d₆) 0.82 (3H, distorted t, CH₃), 1.25 (18H, m. alkylene chain), 2.18 (2H, m, allylic CH₂), 6.37 (2H, distorted s), 6.48 (1H, d, J 15 Hz, C=CHCO₂), 7.52 (4H, AB quartet, J 7.5 Hz, Δν18 Hz, aromatics), 7.60 (1H, d, J 15 Hz, ArCH=C—CO₂) λmax (MeOH) 307 (31,200), 226 (12,200) nm.

Found: C, 80.55; H, 9.91. C₂₂H₃₂O₂ Requires: C, 80.44; H, 9.82%.

Examples 25 to 31 (Table 4) were prepared in a similar manner to that outlined in Example 24.

TABLE 4t

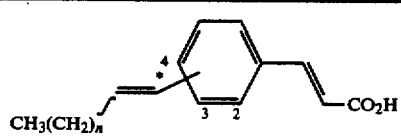

| Example No. | n | Stereochemistry of the asterisked double bond | Position of side chain attachment | m.p. °C. | Recrystalisation solvent | Yield % | Formula | Analysis (calcd/Found) C | H |
|---|---|---|---|---|---|---|---|---|---|
| 25 | 10 | Z | 4 | 96–97 | CH₃OH | 100 | C₂₂H₃₂O₂ | 80.44 | 9.81 |
|    |    |   |   |       |        |     |          | 80.52 | 9.61 |
| 26 | 8  | E | 4 | 112   | CH₃OH | 98  | C₂₀H₂₈O₂ | 79.95 | 9.39 |
|    |    |   |   |       |        |     |          | 80.24 | 9.48 |

TABLE 4t-continued

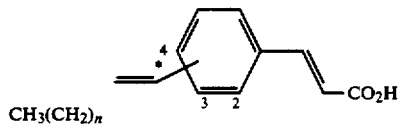

| Example No. | n | Stereochemistry of the asterisked double bond | Position of side chain attachment | m.p. °C. | Recrystalisation solvent | Yield % | Formula | Analysis (calcd/Found) C | H |
|---|---|---|---|---|---|---|---|---|---|
| 27 | 8 | Z | 4 | 94–95 | CH$_3$OH | 87 | C$_{20}$H$_{28}$O$_2$ | 79.95 79.91 | 9.39 9.41 |
| 28 | 12 | E | 4 | 99 | CH$_3$OH | 98 | C$_{24}$H$_{36}$O$_2$ | 80.85 80.92 | 10.18 10.10 |
| 29 | 12 | Z | 4 | 98–99 | CH$_3$OH | 100 | C$_{24}$H$_{36}$O$_2$ | 80.85 80.99 | 10.18 9.99 |
| 30 | 10 | Z | 2 | 83–85 | CH$_3$OH | 100 | C$_{22}$H$_{32}$O$_2$ | 80.44 80.83 | 9.81 10.04 |
| 31 | 10 | Z | 3 | 73–79 | CH$_3$OH | 97 | C$_{22}$H$_{32}$O$_2$ | 80.44 80.46 | 9.81 9.82 |

EXAMPLE 32

Methyl 4-formylcinnamate ethylenedioxy acetal

A mixture of methyl 4-formylcinnamate (15.3 g, 80 mmole, from example 14) and ethane diol (5.5 g) in dry benzene (200 ml) was treated with toluene-p-sulphonic acid (100 mg) and the mixture refluxed under a Dean and Stark head until no further water collected (ca 6 hours). The resulting solution was cooled, evaporated to dryness and the residue recrystallised from methanol-petroleum ether [bp 40°–60°] to give 15.25 g (82%) of material of mp 95°–97° C., $\nu_{max}$ (mull) 1705, 1635, 1440 cm$^{-1}$, δ(CDCl$_3$) 3.60 (3H, s, CH$_3$), 3.86 (4H, s, OCH$_2$—CH$_2$O), 5.68 (1H, s, OCHO), 6.25 (1H, d, J 16.5 Hz, C=CHCO$_2$), 7.28 (4H, m, arom), 7.42 (1H, d, J 16.5 Hz, ArCH=C).

Found; C, 66.40; H, 5.94; C$_{13}$H$_{14}$O$_4$ requires; C, 66.60; H, 6.02%.

EXAMPLE 33

Methyl 3-(4-formylphenyl)propanoate ethylenedioxy acetal

A solution of methyl 4-formylcinnamate ethylenedioxy acetal (15.24 g, 0.065 mole, from example 32) in methanol (200 ml) was hydrogenated over 10% palladinised charcoal (0.5 g) until 1 equivalent of hydrogen was absorbed. The filtered solution was then evaporated to give 15.36 g (100%) of an oil, $\nu_{max}$ (film), 1730, 1610 cm$^{-1}$, δ(CDCl$_3$) 2.54 (2H, m, ArCH$_2$), 2.91 (2H, m, CH$_2$CO$_2$), 3.63 (3H, s, ester CH$_3$), 4.00 (4H, m, OCH$_2$CH$_2$O), 5.72 (1H, s, OCHO), 7.25 (4H, ABq, J 10 Hz, Δν19.5 Hz).

Found; C, 65.49; H, 6.89; C$_{13}$H$_{16}$O$_4$ requires; C, 66.09; H, 6.83%.

EXAMPLE 34

Methyl 3-(4-formylphenyl)propanoate

1M Hydrochloric acid (182 ml) was added to a stirred solution of methyl 3-(4-formylphenyl)propanoate ethylenedioxy acetal (16 g, 68 mmole, from example 33) in tetrahydrofuran (1100 ml) at 0° C. and the mixture stirred overnight at room temperature. The acid was neutralised and the product was extracted into ether. Evaporation of the dried (MgSO$_4$) extracts gave 10.54 g (81%) of the title compound as an oil, $\nu_{max}$ (film) 1735, 1700, 1605 cm$^{-1}$, which was used without further purification.

EXAMPLES 35 AND 36

Methyl 3-{4-[(Z)-1-tridecenyl]phenyl}propanoate (example 35) and methyl 3-{4-[(E)-1-tridecenyl]phenyl}propanoate (example 36)

Sodium hydride (2.88 g, 0.06 mole of a 50% dispersion in mineral oil) was weighed into a dry 250 ml round bottom three necked flask and washed by decantation with petroleum ether. The air was replaced by nitrogen, dry dimethylsulphoxide (30 ml) was added and the mixture was stirred at 75°–80° C. for ca 45 minutes until evolution of hydrogen ceased. The solution was cooled in an ice-water bath and a solution of n-dodecyltriphenylphosphonium bromide (30.6 g, 0.06 mole) in warm dimethylsulphoxide (60 ml) was added. The resulting orange suspension was stirred at room temperature for 10 minutes and a solution of methyl 4-(formylphenyl)propanoate (10.54 g, 0.055 mole) in dimethylsulphoxide (20 ml) was added. The mixture was stirred overnight at room temperature and the product poured into 10% aqueous sodium chloride (1.31) and extracted with hexane. The extracts were washed with water, saturated sodium chloride and dried (MgSO$_4$). Evaporation gave 21.00 g (56%) of (E) and (Z) isomers in the approximate ratio of 15:18 respectively.

Chromatography on silica eluting with petroleum ether [bp 60–80]-dichloromethane (7:3) gave first the pure (Z)-isomer of mp 31°–33° C., $\nu_{max}$ (mull) 1745 cm$^{-1}$, δ(CDCl$_3$) 0.84 (3H, distorted t, terminal CH$_3$), 1.28 (18H, m, alkylene chain), 2.28 (2H, m, allylic CH$_2$), 2.59 (2H, t, ArCH$_2$), 2.92 (2H, t, CH$_2$CO$_2$), 3.68 (3H, s, ester CH$_3$), 5.60 (1H, d.t, J$_d$ 12 Hz, J$_t$ 7.5 Hz, alkyl—CH=C), 6.33 (1H, d, J 12 Hz, ArCH=C), 7.20 (4H, near s, arom).

Found; C, 80.29; H, 10.47; C$_{23}$H$_{36}$O$_2$ requires; C, 80.18; H, 10.53%.

Further elution gave enriched (E) isomer which was chromatographed on 10% argentated silica eluting with petroleum ether [bp 60°–80°]- dichloromethane (7:3) to give pure material of mp 30°–32° C., $\nu_{max}$ (mull) 1750 cm$^{-1}$, δ(CDCl$_3$), 0.83 (3H, distorted t, terminal CH$_3$), 1.28 (18H, m, alkylene chain), 2.15 (2H, m, allylic CH$_2$), 2.57 (2H, distorted t, ArCH$_2$), 2.90 (2H, distorted t, CH$_2$CO$_2$), 3.67 (3H, s, ester CH$_3$), 6.20 (2H, complex m, vinylics), 7.17 (4H, ABq, J 8 Hz, Δν14 Hz, arom).

Found; C, 80.45; H, 10.79; $C_{23}H_{36}O_2$ requires; C, 80.18; H, 10.53%.

EXAMPLE 37

Methyl 3-(2-bromophenyl)propanoate

Methyl iodide (51 g, 22.4 ml, 0.24 mole) was added to a stirred mixture of 3-(2-bromophenyl)propanoic acid (36.7 g, 0.16 mole, prepared as described by F. G. Holliman and F. G. Mann J Chem. Soc. 9, 1960) and anhydrous potassium carbonate (33 g, 0.24 mole) in dry N,N-dimethylformamide (250 ml) and the mixture was stirred at ambient temperature overnight. After removal of the solvent in vacuo the residue was partitioned between ether and water and the ethereal phase washed with aqueous sodium thiosulphate and then brine and dried ($MgSO_4$). Evaporation gave a pale yellow oil which distilled at 116°–118° C. (0.2 mm) to give 36.91 g (95%) of the title ester as a colourless oil, $v_{max}$ 2950, 1740, 1570, 1470, 1440 cm$^{-1}$, $\delta(CDCl_3)$, 2.63 (2H, m, $ArCH_2$), 3.07 (2H, m, $CH_2CO_2$), 3.70 (3H, s, $CH_3$), 7.12 (3H, m, arom), 7.50 (1H, d, arom).

Found; C, 48.97; H, 4.76; Br, 32.62; $C_{10}H_{11}BrO_2$ requires; C, 49.40; H, 4.56; Br, 32.87%.

EXAMPLE 38

Methyl 3-[2-(1-tridecynyl)phenyl]propanoate

Palladium acetate (60 mg) was added to a deaerated solution of methyl 3-(2-bromophenyl)propanoate (11.10 g, 25 mmole), 1-tridecyne (6.75 g) and triphenylphosphine (200 mg) in anhydrous triethylamine (100 ml) and the mixture was stirred at reflux under nitrogen for 24 hrs. After cooling, the precipitated triethylamine hydrobromide was filtered off and the filtrate was evaporated to a red oil. Chromatography on silica eluting with 1:1 dichloromethane-petrol (bp 60°–80° C.) gave the title product, 1.91 g (22%) as an oil, $v_{max}$ (film) 2920, 2850, 1745 cm$^{-1}$, $\delta(CDCl_3)$ 0.84 (3H, distorted t, terminal $CH_3$), 1.28 (18H, m, alkylene chain), 2.39 (2H, t, J 7 Hz; C≡C—$CH_2$), 2.62 (2H, m, $ArCH_2$), 3.04 (2H, m, $CH_2CO_2$), 3.62 (3H, s, ester $CH_3$), 7.12 (3H, m, arom), 7.31 (1H, m, arom).

M$^+$observed 342.2548, calculated for $C_{23}H_{34}O_2$, 342.2559.

EXAMPLE 39

Methyl 3-{2-[(Z)-1-tridecenyl]phenyl}propanoate

A solution of methyl 3-[2-(1-tridecynyl)phenyl]-propanoate (500 mg) in pyridine (20 ml) was hydrogenated at atmospheric pressure over 5% palladium on barium sulphate (20 mg) until 1 equivalent of hydrogen was absorbed. The catalyst was then removed by filtration and the filtrate evaporated to a pale yellow oil. Chromatograpy on silica eluting with 1:1 dichloromethane-petrol (bp 60°–80° C.) gave 390 mg (78%) of the title ester, $v_{max}$ (film) 2930, 2850, 1740 cm$^{-1}$, $\delta(CDCl_3)$, 0.87 (3H, distorted t, terminal $CH_3$), 1.28 (18H, m, alkylene chain), 2.09 (2H, m, allylic $CH_2$), 2.50 (2H, m, $ArCH_2$), 2.90 (2H, m, $CH_2CO_2$), 3.65 (3H, s, ester $CH_3$), 5.70 (1H, d.t, $J_d$ 11.5 Hz, Jt 7.5 Hz, C=CH—R), 6.42 (1H, distorted d, Ar CH=C), 7.17 (4H, m, arom).

M$^+$344.2727, calculated for $C_{23}H_{36}O_2$, 344.2715.

The following carboxylic acids were prepared in near quantitative yield as described in Example 9.

EXAMPLE 40

3-{4-[(Z)-1-Tridecenyl]phenyl}propanoic acid; m.p. ($CH_3OH$) 78°–79° C.

Found; C, 80.10; H, 10.19; $C_{22}H_{34}O_2$ requires; C, 79.95; H, 10.37%.

EXAMPLE 41

3-{4-[(E)-1-Tridecenyl]phenyl}propanoic acid; m.p. ($CH_3OH$) 91° C.,

Found; C, 80.17; H, 10.43; $C_{22}H_{34}O_2$ requires; C, 79.95; H, 10.37%.

EXAMPLE 42

3[2-(1-Tridecynyl)phenyl]propanoic acid; m.p. ($CH_3OH$—$H_2O$) 39°–41° C.,

Found; C, 80.64; H, 10.09; $C_{22}H_{32}O_2$ requires; C, 80.44; H, 9.82%.

EXAMPLE 43

3-{2-[(Z)-1-Tridecenyl]phenyl}propanoic acid; m.p. ($CH_3OH$—$H_2O$) 58°–59° C., Found; C, 79.67; H, 10.71; $C_{22}H_{34}O_2$ requires; C, 79.95; H, 10.37%.

EXAMPLE 44

Methyl 2-(4-formylphenoxy)ethanoate

A solution of 4-hydroxy benzaldehyde, (1.22 g, 0.01 m), methyl glycolate (0.97 g, 0.01 m), and triphenylphosphine, (3.93 g, 0.015 m), in dry tetrahydrofuran, (50 ml) was stirred with cooling in ice and diethylazodicarboxylate, (2.61 g, 0.015 m), added dropwise. The solution was stirred at room temperature for 0.5 hours, then evaporated in vacuo to dryness. Column chromatography of the residue on silica gel eluting with chloroform yielded 1.30 g (67%) of the title compound as an oil which crystallized on standing, mp 39°–41° C., $v_{max}$ (mull) 1750, 1680, 1595, 1575, 1505 cm$^{-1}$.

$\delta(CDCl_3)$ 3.24 (3H, s, ester $CH_3$), 4.76, (2H, s, $OCH_2$) 7.40 (4H, ABq, $v$75 Hz, J 8 Hz, $C_6H_4$), 9.97 (1H, s, CHO).

mass spec Observed mass 194.0577, theoretical mass ($C_{10}H_{10}O_4$).

Found: C, 61.59, H, 4.85, $C_{10}H_{10}O_4$ requires, C, 61.85; H, 5.19%.

EXAMPLE 45

2-(4-methylphenoxy)-ethylcyanide

A solution of 4-methylphenol, (20.0 g 0.185 moles), in acrylonitrile, (150 ml), was treated with benzyltrimethylammonium hydroxide, 40% in methanol (Triton B), (6 ml) and the reaction refluxed for 10 hours, then cooled, and evaporated in vacuo. The residual oil was partitioned between diethyl ether and water and the organic phase separated and washed with water, dilute sodium hydroxide solution, dilute hydrochloric acid, brine and dried ($MgSO_4$). Evaporation of the solvent in vacuo gave 23.44 g of crude product, which was recrystallized from petroleum ether 60°–80° C./diethyl ether to yield 22.93 g, (76%) of pure product as a white crystalline solid, mp 47°–8° C.

$v_{max}$ (mull) 2245, 1890 (weak, 16.13 (shoulder at 1625), 1590, 1518 cm$^{-1}$. $\delta(CDCl_3)$ 2.28 (3H, s, $CH_3$), 2.73 (2H, t, J 6 Hz, $CH_2CH$), 4.12 (2H, t, J 7 Hz, $OCH_2$) 6.92 (4H, ABq, $v$29 Hz, J9 Hz, $C_6H_4$).

Mass spec. Observed mass 161.0838, theoretical mass 161.0842 for $C_{10}H_{11}NO$.

Found: C, 74.37; H, 6.64; N, 9.17; $C_{10}H_{11}NO$ requires C, 74.51; H, 6.90; N, 8.69%.

EXAMPLE 46

Methyl 3-(4-methylphenoxy)-propanoate 2-(4-methylphenoxy)ethyl cyanide (20.0 g, 0.125 moles) was dissolved in 10% methanolic concentrated sulphuric acid (200 ml) and the solution refluxed for 48 h, then cooled and evaporated in vacuo to a low volume. The residue was partitioned between diethyl ether and water and the organic phase separated and washed with water, brine and dried ($MgSO_4$). Evaporation in vacuo yielded 22.04 g of the crude product as a colourless oil. Distillation at 0.08 mm/Hg afforded 18.74 g, (78%) of the pure ester as a colourless oil, bp 103° C. $\nu_{max}$, (film), 1745, 1618, 1590, 1518 $cm^{-1}$ $\delta(CDCl_3)$, 2.27 (3H, s, $ArCH_3$) 2.74 (2H, t, J6 Hz, $CH_2CO_2$) 3.70 (3H, s, ester $CH_3$) 4.16 (2H, t, J6 Hz, $OCH_2$), 6.90 (4H, ABq, $\Delta\nu$26 Hz, J9 Hz, $C_6H_4$)

Mass spec. Observed mass 194.0944, theoretical mass for $C_{11}H_{14}O_3$ 194.0943.

Found C, 68.28; H, 7.12, $C_{11}H_{14}O_3$ requires C, 68.02; H, 7.28%.

EXAMPLE 47

Methyl 3-(4-formylphenoxy)-propanoate

A solution of methyl 3-(4-methylphenoxy)-propanoate, (15.0 g, 0.077 moles) in acetonitrile, (270 ml), was added to a solution of potassium peroxydisulphate, (41.60 g, 0.154 moles) and copper (II) sulphate (3.85 g, 0.015 moles) in water, (270 ml). The resulting mixture was stirred at 65°–70° C. for 3.5 h, then cooled and extracted with diethyl ether. The organic extract was washed with water, saturated brine and dried, ($MgSO_4$). Evaporation of the solvent gave 14.83 g of an orange oil which was distilled at 0.1 mm/Hg to yield 7.40 g (47%) of the title compound as an oil which crystallized, mp 48°–50° C., $\nu$max (mull) 1735, 1680, (shoulder at 1685), 1605, 1580, 1515 $cm^{-1}$ $\delta(CDCl_3)$ 2.81 (2H, t, J 6 Hz, $CH_2CO_2$) 3.72 (3H, S, $CH_3$) 4.30 (2H, t, J6 Hz $OCH_2$) 7.39 (4H, ABq, $\Delta\nu$75 Hz, J9 Hz $C_6H_4$) 9.90 (1H, s, CHO).

Mass spec. Observed mass, 208.0737, theoretical mass 208.0736 for $C_{11}H_{12}O_4$ Found, C, 63.30; H, 5.83; $C_{11}H_{12}O_4$ requires C, 63.45; H, 5.81%.

EXAMPLE 48

Ethyl 4-(4-formyl phenoxy)-butanoate

A solution of 4-hydroxybenzaldehyde (15.0 g, 0.122 mole) in butanone (200 ml) was treated with anhydrous potassium carbonate (18.55 g, 0.134 mole), and the mixture stirred at room temperature for 20 mins. Ethyl 4-bromobutanoate, (24.0 g, 0.122 mole), dissolved in butanone (10 ml), was added dropwise to the stirred mixture over a period of 1 h. The reaction was stirred and refluxed for 6 h, then cooled and partitioned between water and butanone. The organic phase was separated, washed with dilute sodium hydroxide, water, brine and dried, ($MgSO_4$). Evaporation of the solvent in vacuo gave a red oil, which was distilled at 0.05 mm/Hg to yield 19.31 g (67%) of a colourless oil, bp 152°–6° C. $\nu_{max}$ (film) 1730, 1685, 1600, 1580, 1508 $cm^{-1}$ $\delta$ ($CDCl_3$) 1.25 (3H, t, J 7 Hz, ester $CH_3$) 2.18 (2H, bt, J6 Hz, $OCH_2\underline{CH_2}$), 2.49 (2H, bt, J6 Hz, $CH_2CO_2$), 4.09 (2H, t, J6 $\overline{Hz}$, $OCH_2$), 4.11 (2H, q, J7 Hz, ester $CH_2$), 7.38 (4H, ABq, $\Delta\nu$75 Hz, J9 Hz, $C_6H_4$), 9.90 (1H, s, CHO)

Mass spec. Observed mass 236.1049, theoretical mass 236.1049 for $C_{13}H_{16}O_4$ Found C, 66.15; H, 6.87; $C_{13}H_{16}O_4$ requires C, 66.09, H, 6.83%.

EXAMPLE 49

Methyl (2-formyl phenoxy)-propanoate

This compound was prepared by the route described in Examples 45–47, starting from o-cresol.

mp 44° $\nu_{max}$ (mull) 1750, 1695, 1600, 1240, 1040 $cm^{-1}$ $\delta(CDCl_3)$ 2.88 (2H, t, $CH_2CO_2$), 3.75 (3H, s, ester $CH_3$) 4.40 (2H, t, O $CH_2$) 7.50 (4H, m, arom.), 10.48 (1H, s, CHO)

Found C, 63.49, H, 5.75% $C_{11}H_{12}O_4$ requires C, 63.45, H, 5.81%.

Observed mass 208.0737 Theoretical mass 208.0736 ($C_{11}H_{12}O_4$).

EXAMPLES 50 AND 51

(E) and (Z) methyl 2-[4-(1-tridecenyl)phenoxy]ethanoate

Sodium hydride (2.40 g, 0.052 m of a 50% dispersion in oil) was washed by decantation with petroleum ether bp 60°–80° C. and added to dry, deaerated dimethylsulphoxide, (100 ml), under nitrogen. The mixture was stirred at 75° C. for 0.75 hours, until no more hydrogen evolved. The solution was cooled to 5° C. in an ice bath, and a solution of n-dodecyl triphenylphosphonium bromide, (25.60 g, 0.05 m) in dry, deaerated dimethylsulphoxide, (50 ml) was added with stirring. The resulting solution was stirred at room temperature for 10 minutes, and a solution of methyl 2-(4-formylphenoxy)-ethanoate, (10.0 g. 0.051 m) in dry dimethylsulphoxide (50 ml), was added dropwise. The reaction mixture was stirred for 6 hours at room temperature, then poured into 10% brice and extracted with n-hexane. The hexane extracts were washed with water, saturated brine and dried, ($MgSO_4$). Evaporation in vacuo gave 10.0 g of a yellow oil, which gave a mixture of E/Z isomers, 1.50 g (9%) after chromatography on silica gel eluting with dichloromethane.

The isomers were separated by chromatography on silica gel eluting with dichloromethane-petroleum ether bp 60°–80° C., (1:1). The Z-isomer, (0.414 g) was eluted first as a white crystalline solid mp ($CCl_4$/petroleum ether bp 60°–80° C.) 58.9° C., followed by a mixture of isomers and finally the E-isomer (0.140 g) as a white crystalline solid, mp (petroleum ether, bp 60°–80° C.) 55°–7° C.

EXAMPLE 50

(Z) Methyl 2-[4-(1-tridecenyl)phenoxy]-ethanoate $\nu_{max}$ (mull) 1775, 1608, 1510 $cm^{-1}$ $\delta(CDCl_3)$ 0.88 (3H, m, terminal $CH_3$), 1.30 (18H, m, ($CH_2$) q), 2.25 (2H, m, allylic $CH_2$), 3.81 (3H, s, ester $CH_3$) 4.63 (2H, s, $OCH_2$) 5.52 (1H, d.t, Jd 12 Hz, Jt 7 Hz, =CH—alkyl), 6.32 (1H, d, J 12 Hz, ArCH=), 7.04 (4H, ABq, $\nu$28 Hz, J 9 Hz, $C_6H_4$).

Mass spec. Observed mass 346.2509, theoretical mass 346.2508 ($C_{22}H_{34}O_3$).

Found: C, 76.21; H, 9.35; $C_{22}H_{34}O_3$ requires C, 76.26, H 9.89%.

EXAMPLE 51

(E) methyl 2-[4-(1-tridecenyl)phenoxy]-ethanoate $v_{max}$ (mull) 1770, 1605, 1515 cm$^{-1}$. δ(CDCl$_3$) 0.88 (3H, m, terminal CH$_3$) 1.26 (18H, m, (CH$_2$) q), 2.19 (2H, m, allylic CH$_2$), 3.80 (3H, s, ester CH$_3$) 4.62 (2H, s, OCH$_2$) 6.05 (1H, d.t, Jd 16 Hz, =CH—alkyl), 6.35 (1H, d, J 16 Hz, ArCH=), 7.05 (4H, ABq, $v$ 35.5 Hz, J 9 Hz, C$_6$H$_4$).

Mass spec. Observed mass 346.2513, theoretical mass 346.2502, (C$_{22}$H$_{34}$O$_3$).

Found: C, 76.66, H, 10.08, C$_{22}$H$_{34}$O$_3$ requires C, 76.26; H, 9.89%.

Examples 52 to 57 (Table 5) were prepared in a similar manner to that described in Examples 50 and 51.

TABLE 5

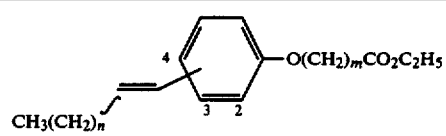

| Example No. | n | m | Stereochemistry of the double bond | Position of side chain attachment | mp °C. | Recrystalisation solvent | Yield % | Formula | Analysis (calcd/Found) C | H |
|---|---|---|---|---|---|---|---|---|---|---|
| 52 | 8 | 3 | E | 4 | 42–43 | C$_2$H$_5$OH | ⎫ 52 | C$_{23}$H$_{36}$O$_3$ | 76.62 76.46 | 10.07 9.94 |
| 53 | 8 | 3 | Z | 4 | oil | — | ⎭ | C$_{23}$H$_{36}$O$_3$ | 76.62 76.92 | 10.07 9.92 |
| 54 | 10 | 3 | E | 2 | oil | — | ⎫ 50 | C$_{25}$H$_{40}$O$_3$ | | |
| 55 | 10 | 3 | Z | 2 | oil | — | ⎭ | C$_{25}$H$_{40}$O$_3$ | 77.27 77.35 | 10.38 10.38 |
| 56 | 7 | 3 | E | 2 | oil | — | ⎫ 21 | C$_{22}$H$_{34}$O$_3$ .0.5H$_2$O | 74.32 74.51 | 9.92 9.63 |
| 57 | 7 | 3 | Z | 2 | oil | — | ⎭ | C$_{22}$H$_{34}$O$_3$ .0.5H$_2$O | 74.32 74.60 | 9.92 9.99 |

EXAMPLES 58 AND 59

(E) and (Z) Methyl 3-[4-(1-dodecenyl)phenoxy]-propanoate

A mixture of n-undecyltriphenylphosphonium bromide (4.95 g, 9.94 mmole), in dry, deaerated diethyl ether (100 ml) under nitrogen was vigorously stirred at 0° C. and n-butyl lithium, 1.6 moles in hexane (5.40 ml, 8.65 mmole) added dropwise. The reaction was stirred for 20 mins at 0° C. and then a solution of methyl 3-(4-formylphenoxy)propanoate, (1.80 g, 8.65 mmole) in dry diethyl ether was added dropwise. The reaction was stirred at 0° C. for 0.75 h, then poured into 2.5M hydrochloric acid (200 ml) and extracted with diethyl ether (two times). The combined organic extracts were washed with water (two times), dried, (MgSO$_4$), and evaporated in vacuo to give 2.78 g of a creamy oil, which gave a 2:3 mixture of E/Z isomers, 0.879 l g, (30%) after chromatography on silica gel eluting with dichloromethane/n-hexane (1:1).

The isomers were separated by column chromatography on silica gel, eluting with dichloromethane/petroleum ether, bp 60°–80° C., (1:4). The Z-isomer, (214 mg), was eluted first as a colourless oil, followed by a mixture of isomers, (437 mg), and finally the E-isomer, (200 mg) was eluted as a colourless oil.

EXAMPLE 58

(E) Methyl 3-[4-(1-dodecenyl)phenoxy]-propanoate $v_{max}$ (mull) 1743, 1605, 1575 (weak) 1510 cm$^{-1}$ δ(CDCl$_3$), 0.88, (3H, bt, J6 Hz, terminal CH$_3$) 1.26, (16H, m, (CH$_2$)$_8$), 2.14 (2H, bt, J6 Hz, allylic CH$_2$), 2.79 (2H, t, J6 Hz, CH$_2$CO$_2$), 3.72 (3H, s, ester CH$_3$), 4.24 (2H, t, J6 Hz, OCH$_2$), 6.04, (1H, d.t, J$_d$15.5 Hz, J$_t$ 6 Hz, =CH—alkyl), 6.34 (1H, d, J 15.5 Hz, Ar—CH=), 7.03 (4H, ABq, Δ$v$35 Hz, J9 Hz, C$_6$H$_4$)

Mass spec. Observed mass 346.2510, theoretical mass 346.2508 for C$_{22}$H$_{34}$O$_3$ Found, C, 76.54; H, 9.98; C$_{22}$H$_{34}$O$_3$ requires C, 76.26; H, 9.89%.

EXAMPLE 59

(Z) Methyl 3-[4-(1-dodecenyl)phenoxy]-propanoate $v_{max}$, (film) 1743, 1605, 1570, (weak), 1505 cm$^{-1}$ δ, (CDCl$_3$), 0.88 (3H, bt, J6 Hz, terminal CH$_3$), 1.26 (16H, m, (CH$_2$)$_8$), 2.26 (2H, bt, J6 Hz, allylic CH$_2$), 2.80 (2H, t, J6 Hz, CH$_2$CO$_2$), 3.73 (3H, s, ester CH$_3$), 4.26 (2H, t, J6 Hz, OCH$_2$), 5.57 (1H, d.t, J$_d$ 12 Hz, J$_t$ 7 Hz =CH—alkyl), 6.34 (1H, d, J 12 Hz, Ar—CH=), 7.03 (4H, ABq, Δ$v$25 Hz, J9 Hz, C$_6$H$_4$).

Mass spec. Observed mass 346.2510, theoretical mass 346.2508 for C$_{22}$H$_{34}$O$_3$ Found, C, 76.16; H, 10.17; C$_{22}$H$_{34}$O$_3$ requires C, 76.26; H, 9.89%.

EXAMPLE 60

(Z) 2-[2-(1-tridecenyl)-phenoxy]ethanoic acid

Dodecyltriphenyl phosphonium bromide (4.09 g, 0.008 mole) was suspended in dry ether (50 ml) and stirred under nitrogen. The mixture was cooled in ice and a solution of n-butyl lithium (1.6M in hexane) was added until a faint yellow colour persisted (1.5 ml). A further amount of the n-butyl lithium solution (5.0 ml, 0.007 mole) was then added. The mixture was stirred at 0°/0.25 hr, when a solution of methyl(2-formylphenoxy)ethanolate (1.16 g, 0.006 mole) in dry ether (10 ml) was added dropwise. The reaction was stirred at 10°/3 hr, poured into water and extracted with ether. The solvent extracts were combined and washed with dilute hydrochloric acid and water. After drying (MgSO$_4$), the solvent was evaporated to give a yellow oil (3.02 g). HPLC showed the presence of two sets of peaks, which were identified as the (E) and (Z) methyl esters (faster running) and the (E) and (Z) butyl esters (slower running). Rapid chromatography on coarse silica (CH$_2$Cl$_2$)

gave the mixed esters (1.14 g). Rechromatography on Kieselgel 60 (CH$_2$Cl$_2$-petroleum ether 60°-80°, 40:60) separated the ethyl and butyl esters. The mixed (E) and (Z) ethyl esters (0.81 g) were hydrolysed by heating at 90°/0.5 hr with 1.25M sodium hydroxide solution (10 ml) and ethanol (5 ml). Acidification yielded the mixed isomer acids (0.67 g), which on crystallization from petroleum ether 60°-80° gave the pure (Z) acid m.p. 82° (0.31 g) identical with the material produced in Example 79.

Found C, 73.73, H, 9.70% C$_{21}$H$_{32}$O$_3$ 0.5H$_2$O requires C, 73.85, H, 9.74%.

The following compounds were prepared by the method described in Example 60.

EXAMPLE 61

(Z) 3-[2-(1-tridecenyl)phenoxy]-propanoic acid m.p. 69° $\upsilon_{max}$ (mull) 1715, 1600, 1220, 1040, 745 cm$^{-1}$ δ(CDCl$_3$) 0.80 (3H, distorted t, terminal CH$_3$), 1.25 (18H, s, alkylene chain) 2.20 (2H, q, allylic CH$_2$), 2.80 (2H, t, CH$_2$CO$_2$), 4.20 (2H, t, OCH$_2$), 5.67 (1H, d.t, J$_d$ 12 Hz, J$_t$ 7 Hz, =CHalkyl), 6.42 (1H, d, J12 Hz ArCH=) 7.10 (4H, m, arom.).

Found C, 75.29, H, 9.64% C$_{22}$H$_{34}$O$_3$ 0.25 H$_2$O requires C, 75.27, H, 9.90%.

Mass spec. Observed mass 346.2513.

Theoretical mass 346.2508 (C$_{22}$H$_{34}$O$_3$).

EXAMPLE 62

(Z) 4-[2-(1-tridecenyl)phenoxy]-butanoic acid

The reaction of dodecyltriphenyl phosphonium bromide (4.09 g, 0.008 mole) with ethyl(2-formylphenoxy)-butanoate (1.41 g, 0.006 mole) in the presence of n-butyl lithium, gave after one chromatographic separation, a yellow oil (2.37 g). This oil was hydrolysed with a solution of lithium hydroxide monohydrate (2.56 g) in a mixture of tetrahydrofuran and water (120 ml, 1:1). Acidification gave the crude mixed isomer acid (1.48 g). Crystallization from hexane gave the pure (Z) acid m.p. 54° (0.61 g) whose physical properties were the same as the material obtained in Example 84.

EXAMPLE 63-64

Dodecyltriphenyl phosphonium bromide (8.18 g, 0.016 mole) was reacted with ethyl 5-(2-formylphenoxy)-pentanoate (2.86 g, 0.011 mole) as described in Example 60. Separation of the crude mixed esters by chromatography gave Examples 63-64.

EXAMPLE 63

(E) n-Butyl 5-(2-(1-tridecenyl)phenoxy)-pentanoate oil, $\upsilon_{max}$ (film) 1730, 1595, 1450, 1240, 740 cm$^{-1}$ δ(CDCl$_3$), 0.80 (3H, t, terminal alkylene CH$_3$), 0.90 (3H, t, terminal ester CH$_3$), 1.30 (20H, m, alkylene chain +ester CH$_2$CH$_3$), 1.85 (6H, m, OCH$_2$CH$_2$CH$_2$+ester CO$_2$CH$_2$CH$_2$). 2.33 (4H, m, allylic CH$_2$+CH$_2$CO$_2$), 4.05 (4H, m, OCH$_2$+ester CO$_2$CH$_2$). 6.18 (1H, d.t, J$_d$ 16 Hz, J$_t$ 7 Hz,=CHalkyl). 6.70 (1H, d, J16 Hz, ArCH=) 7.10 (4H, m, arom.)

Found C, 77.81, H, 11.00% C$_{28}$H$_{46}$O$_3$ requires C, 78.09, H, 10.77%.

Observed mass 430.3452 Theoretical mass 430.3447 (C$_{28}$H$_{46}$O$_3$).

EXAMPLE 64

(Z) Ethyl 5-[2-(1-tridecenyl)phenoxy]-pentanoate oil, δ(CDCl$_3$) 0.83 (3H, distorted t, terminal CH$_3$), 1.25 (21H, m, alkylene chain+ester CH$_3$), 1.80 (4H, m, OCH$_2$CH$_2$CH$_2$), 2.25 (4H m, allylic CH$_2$+CH$_2$CO$_2$), 4.05 (4H, m, ester CH$_2$+OCH$_2$). 5.65 (1H d.t, J$_d$ 12 Hz, J$_t$ 7 Hz, =CHalkyl), 6.52 (1H, d, J12 Hz, ArCH=) 7.05 (4H, m, arom.).

Found C, 76.58, H, 10.86% C$_{26}$H$_{42}$O$_3$ 0.25H$_2$O requires C, 76.70, H, 10.52%.

Observed mass 402.3132 Theoretical mass 402.3134 (C$_{26}$H$_{42}$O$_3$).

EXAMPLE 65

Ethyl 4-(2-hydroxymethylphenoxy)-butyrate

Ethyl 4-(2-formylphenoxy)-butyrate was prepared by the method described in British Pat. No. 1,350,883. The ester (5.00 g) was dissolved in methanol (100 ml) and cooled to 15° C. A solution of sodium borohydride (1.00 g) in water (10 ml) containing 2 drops of 1M sodium hydroxide solution was added dropwise with stirring, at such a rate that the temperature of the reaction stayed between 15°-20° C. After 0.5 hr the methanol was evaporated, the residue dissolved in ether. The solution was washed with water, dried and evaporated to yield 4.55 g crude product.

Distillation under reduced pressure gave the pure hydroxymethyl compound as a fraction boiling at 162°-4°/0.8 mm/Hg.

$\upsilon_{max}$ (film) 3425, 1725, 1600, 1240, 1040, 755 cm$^{-1}$. δ(CDCl$_3$) 1.25 (3H, t, ester CH$_3$), 2.18 (2H, q, CH$_2$CO$_2$) 2.53 (2H, t, OCH$_2$CH$_2$), 3.90 (4H, m, OCH$_2$+ester CH$_2$) 4.65 (2H, d, CH$_2$OH, collapses to s with D$_2$O), 7.10 (4H, m, arom.)

Found C, 65.82, H, 7.82% C$_{13}$H$_{18}$O$_4$ requires C, 65.53, H, 7.61%.

Observed mass 238.1212 (C$_{13}$H$_{18}$O$_4$).

EXAMPLE 66

Ethyl 4-(2-bromomethylphenoxy)-butyrate

The hydroxymethyl compound (Example 65) (2.40 g) and carbon tetrabromide (3.20 g) were dissolved in dry dichloromethane (50 ml). The mixture was cooled in ice water and a solution of triphenylphosphine (3.20 g) in dichloromethane (15 ml) was added in portions over 10 min. The mixture was stirred at 0°/4 hr and the solvent was evaporated. The residual gummy solid was chromatographed on Kieselgel 60 (CH$_2$Cl$_2$). The product was eluted in the first fractions (2.62 g).

Oil, $\upsilon_{max}$ (film) 1730, 1600, 1490, 1250, 1040, 750 cm$^{-1}$ δ(CDCl$_3$), 1.25 (3H, t, ester CH$_3$), 2.18 (2H, q, CH$_2$CO$_2$) 2.55 (2H, t, OCH$_2$CH$_2$), 4.10 (4H, m, OCH$_2$+ester CH$_2$) 4.55 (2H, s, CH$_2$Br), 7.10 (4H, m, arom.).

Observed mass 300.0357 (C$_{13}$H$_{17}$BrO$_3$).

Found C, 51.79; H, 5.69; Br. 26.65% C$_{13}$H$_{17}$BrO$_3$ requires C, 51.84, H, 5.64, Br. 26.53%.

EXAMPLE 67

(E) Ethyl 4-[2-(1-undecenyl)phenoxy]-butanoate

Equimolar amounts of the benzylbromide (Example 66) and triphenylphosphine were refluxed in toluene for 3 hr. The white solid which precipitated was collected, washed with dry ether and dried. (92% yield).

The above triphenylphosphonium salt (7.96 g) was added to the reaction product of sodium hydride (50%, 0.68 g) and dimethyl sulphoxide (15 ml), with stirring under nitrogen. After 0.25 hr decaldehyde (2.20 g) in dry DMSO (10 ml) was added and the mixture stirred at 0°–5° for 3 hr. The product was isolated as described in Example 50/51. Yield 2.45 g (E) and (Z) esters, containing approximately 75% (E) isomer. Chromatography on Kieselgel 60 (dichloromethane:hexane, 1:4) gave the pure (E) ester.

oil $\nu_{max}$ (film) 1730, 1600, 1450, 1240, 1050, 740 cm$^{-1}$ δ(CDCl$_3$) 0.88 (3H, distorted t, terminal CH$_3$), 2.27 (17H, m, alkylene chain+ester CH$_3$), 2.22 (4H, m, allylic CH$_2$+CH$_2$CO$_2$) 2.50 (2H, t, OCH$_2$CH$_2$), 4.15 (4H, m, OCH$_2$+ester CH$_2$) 6.20 (1H, d.t, J$_d$ $\overline{16}$ Hz, J$_t$7 Hz, =CHalkyl), 6.62 (1H, d, J16 Hz, ArCH=) 7.10 (4H, m, arom.).

Found C, 76.54, H, 10.40% C$_{23}$H$_{36}$O$_3$ requires C, 76.62, H, 10.05%.

EXAMPLES 68 AND 69

(E) and (Z) Ethyl 4-[2-(1-tridecenyl)phenoxy)-butanoate

The compounds of Examples 54 and 55 can also be prepared by the method of Le Bigot, Delmas and Gaset (Syn. Com. 12, 1115, 1982).

(a) Dodecyltriphenylphosphonium bromide (6.38 g, 0.0125 mole) potassium carbonate (1.75 g, 0.0125 mole) and ethyl(2-formylphenoxy)butanoate (2.36 g, 0.01 mole) were stirred and refluxed in 1,4-dioxan (15 ml). After 3 hr the reaction was filtered and the solvent evaporated to yield a dark gum. Extraction with boiling ether (3×) gave a yellow oil (3.21 g). Chromatography on coarse Kieselgel yielded the mixed isomer esters (2.14 g). Examination by HPLC showed a preponderance of the (Z) isomer (approx 70%) compared with the 50—50 ratio normally obtained in the reaction described in Example 50/51. Chromatography on Kieselgel 60 (CH$_2$Cl$_2$-hexane, 1:4) separated the (E)–(Z) isomers which had the properties described in Examples 54 and 55.

(b) In a reaction similar to (a) above but using methanol as the solvent instead of 1,4-dioxan, the crude product was shown to contain approx. 75% of the (E) isomer, again separation by chromatography yielded the (E)–(Z) isomers identical with the material obtained in Examples 54 and 55.

EXAMPLE 70

Ethyl(2-bromophenoxy)-butanoate

2—Bromophenol (17.30, 0.1 mole), potassium carbonate (15.2 g, 0.11 mole) were stirred and refluxed in butanone for 0.25 hr. Ethyl 4-bromobutanoate (17.50 g, 0.1 mole) was then added and the reaction refluxed for 18 hr. The inorganic material was removed by filtration, and the solvent was evaporated. The residue was dissolved in ether, washed with dilute sodium hydroxide solution and water, dried and evaporated to yield 24.32 g crude product. Distillation at 122°–4°/0.1 mm/Hg yielded the pure ester 20.74 g.

$\nu_{max}$ 1735, 1595, 1490, 1470, 1050, 1030, 745 cm$^{-1}$ δ(CDCl$_3$) 1.18 (3H, t, ester CH$_3$), 2.20 (2H, q, CH$_2$CO$_2$), 2.58 (2H, t, OCH$_2$CH$_2$) 4.12 (4H, t+q, OCH$_2$+ester CH$_2$), 7.20 (4H, m, arom).

EXAMPLE 71

(E) Ethyl 4-[2-(1-dodecenyl)-phenoxy]butanoate

Ethyl(2-bromophenoxy)-butanoate (1.33 g, 0.005 mole), 1-dodecene (0.85 g 0.005 mole) and tri(o-tolyl)-phosphine (52 mg) were dissolved in ethyldiisopropylamine (15 ml) and stirred and warmed under vacuum to remove oxygen. The atmosphere was replaced with argon, and palladium acetate (15 mg) was added. The reaction was stirred at 100° for 30 hr. Further quantities of 1-dodecene (0.42 g) were added to the reaction after 6 and 24 hrs. After 30 hrs the mixture was poured into dilute hydrochloric acid, the product extracted into ether. The solvent extracts were washed with water and dried. Evaporation gave the crude product as a pale oil. Chromatography on Kieselgel 60 gave the title compound as the (E)-isomer admixed with some unidentified material.

EXAMPLE 72

(Z) 3-(1-Dodecenyl)phenol

Sodium hydride (1.80 g, 0.037M of a 50% dispersion in oil), was washed by decantation with petroleum ether, bp 60°–80° C. and added to dry, deaerated dimethylsulphoxide (40 ml) under nitrogen. The mixture was stirred at 75° C. for 0.75 h, cooled to 5° C. in an ice bath and a solution of n-undecyltriphenyl phosphonium bromide (18.60 g 0.037M) in dimethylsulphoxide, (40 ml) added. The red solution was stirred for 15 min, and then treated dropwise with 3-hydroxy benzaldehyde, sodium salt, [4.57 g of 3-hydroxy benzaldehyde, in dimethylsulphoxide, (40 ml), treated with one molar equivalent of sodium hydride] at 10° C. After stirring at 10° C. for 1 h and at room temperature for 3 h, the pale brown mixture was poured into 10% brine, (600 ml), acidified with dilute hydrochloric acid and extracted with hexane (twice). The combined organic phases were washed with water (twice) brine and then dried, (MgSO$_4$). Evaporation of the solvent and purification by column chromatography using silica gel and dichloromethane/hexane [1:1] as eluent, yielded 4.00 g (42%) of the single Z isomer as a pale yellow oil.

$\nu$max (film) 3320, 1608, 1580, 1490 cm$^{-1}$ δ(CDCl$_3$) 0.84 (3H, bt, terminal CH$_3$), 1.28 (16H, m, (CH$_2$)$_8$), 2.23 (2H, bt, J 7 Hz, allylic CH$_2$), 4.83 (1H, s, OH), 5.60 (1H, d.t, Jd $\overline{12}$ Hz, J$_t$7 Hz, =CH—alkyl) 6.32 (1H, d, J 12 Hz, ArCH=), 6.74 (3H, m, arom), 7.16 (1H, m, arom).

Found: C, 81.72; H, 10.86; C$_{18}$H$_{28}$O.0.25H$_2$O requires: C, 81.64; H, 10.85%.

Mass Spec. Observed mass 260.2127, theoretical mass 260.2140 for C$_{18}$H$_{28}$O.

EXAMPLE 73

(E) 2-(1-Octenyl)-phenol

A suspension of n-heptyltriphenylphosphonium bromide (25.00 g, 0.057 mole), in dry, deaerated tetrahydrofuran (150 ml) was vigorously stirred at 5° C. under nitrogen and n-butyl lithium, 1.55 molar in hexane (46.6 ml, 0.073 mole, 1.3 equivalents), added dropwise. The reaction was stirred for 20 mins at 5° C., then treated dropwise with a suspension of sodium salicylaldehyde [prepared from salicylaldehyde (6.33 g, 0.052 moles) and one molar equivalent of sodium hydride in dry, deaerated THF (150 ml) under nitrogen] at 10° C. After stirring at 10° C. for 1 h, the reaction was poured into water (500 ml), acidified with dilute hydrochloric acid and extracted twice with diethyl ether. The combined organic extracts were washed with water (twice) and dried, (MgSO$_4$). Evaporation of the solvent in vacuo yielded a pale yellow oil, which was purified by column chromatography using silica gel, eluting with dichloromethane/hexane [1:1] to give 6.14 g (58%) of the single E isomer as a pale yellow oil.

νmax (film) 1495, 1575, 1605, 3400 cm$^{-1}$. δ(CDCl$_3$) 0.88, (3H, distorted t, terminal CH$_3$), 1.34 (8H, m, (CH$_2$)$_4$), 2.20 (2H, m, allylic CH$_2$), 4.93, (1H, s, OH, exchanged with D$_2$O), 6.14 (1H, d.t, J$_d$ 16 Hz, J$_t$ 6 Hz, =CH—alkyl), 6.54 (1H, d, J 16 Hz, Ar—CH=), 7.01 (4H, m, arom, Hs).

Found: C, 80.61; H, 9.84; C$_{14}$H$_{20}$O.0.25H$_2$O requires: C, 80.53; H, 9.96%.

Mass Spec. Observed mass 204.1530, theoretical mass 204.1514 for C$_{14}$H$_{20}$O.

EXAMPLE 74

(Z) and (E) 2-(1-Octenyl)-phenol

The title compounds were prepared using the same procedure as in Example 72, using 0.052M of salicylaldehyde to yield 8.91 g (85%) of the isomeric mixture which was separated by chromatography on silica gel, eluting with n-hexane/dichloromethane, [4:1]. The Z-isomer (5.44 g) as eluted first, followed by a mixture of isomers and finally the E isomer (2.32 g) was eluted.

Data: (Z) 2-(1-Octenyl)-phenol

νmax (film) 3480, 1605, 1577, 1485, 1450 cm$^{-1}$ δ(CDCl$_3$) 0.85 (3H, distorted t, terminal CH$_3$), 1.27 (8H, m, (CH$_2$)$_4$), 2.08 (2H, m, allylic CH$_2$), 5.03 (1H, s, OH, exchanged D$_2$O), 5.91 (1H, d.t, J$_d$ 12 Hz, =CH—alkyl) 6.38 (1H, d, J 12 Hz, ArCH=), 7.04 (4H, m, arom Hs).

Found: C, 80.71; H, 9.80; C$_{14}$H$_{20}$O, 0.25H$_2$O requires: C, 80.53; H. 9.96%.

Mass Spec. Observed Mass. 204.1499, theoretical mass 204.1514 for C$_{14}$H$_{20}$O.

EXAMPLE 75

(Z) Ethyl 4-[3-(1-dodecenyl)phenoxy]-butanoate (Z) 3-(1-Dodecenyl)-phenol, (1.00 g 3.84 mmole) was dissolved in butanone, (50 ml), and anhydrous potassium carbonate, (0.584 g, 4.20 mmole) added. After stirring for 0.5 h at room temperature, ethyl 4-bromobutanoate, (0.750 g, 3.84 mmole) was added and the reaction stirred and refluxed for 36 h, then cooled. The mixture was poured into water (50 ml) and extracted with diethyl ether, the organic phase was separated and washed with water, (twice), dried, (MgSO$_4$) and evaporated in vacuo to yield 1.37 g of the crude product as an oil. Purification by column chromatography, using silica gel and eluting with dichloromethane/hexane [1:1] gave 1.15 g (71%) of pure product as a colourless oil.

νmax (film) 1640, 1605, 1598, 1575 cm$^{-1}$. δ(CDCl$_3$) 0.87 (3H, distorted t, terminal CH$_3$), 1.27 (16H, m, (CH$_2$)$_8$), 1.33 (3H, t, J 7 Hz, ester CH$_3$), 2.15 (4H, m, OCH$_2$CH$_2$+allylic CH$_2$), 2.50 (2H, t, J 6 Hz, CH$_2$CO$_2$), 3.99 (2H, t, J 6 Hz, OCH$_2$), 4.12 (2H, q, J 7 Hz, ester CH$_2$), 5.63 (1H, d.t, J$_d$ 12 Hz, J$_t$ 7 Hz=CH—alkyl), 6.36 (1H, d, J 12 Hz, ArCH=), 6.80 (3H, m, arom Hs), 7.19 (1H, arom H).

Found: C, 76.69; H, 10.34; C$_{24}$H$_{38}$O$_3$ requires: C, 76.95; H, 10.23%.

Mass Spec. Observed mass 374.2820, theoretical mass 374.2821 for C$_{24}$H$_{38}$O$_3$.

The following esters were prepared as described in Example 75:

EXAMPLE 76

(E) Ethyl 4-[2-(1-octenyl)-phenoxy]-butanoate; oil, Found; C, 75.83; H, 9.61; C$_{20}$H$_{30}$O$_3$ requires; C, 75.43; H, 9.50%.

EXAMPLE 77

(Z) Ethyl 4-[2-(1-octenyl)-phenoxy]-butanoate; oil, Found: C, 74.31; H, 9.55; C$_{20}$H$_{30}$O$_3$.0.25H$_2$O requires; C, 74.37; H, 9.52%.

EXAMPLE 78

(E) 4-[4-(1-undecenyl)phenoxy]-butanoic acid (E) Ethyl 4-[4-(1-undecenyl)phenoxy]-butanoate, (175 mg, 0.49 mmole) was dissolved in dry THF (10 ml) and water (5 ml) and treated with a solution of lithium hydroxide monohydrate (200 mg, 4.9 mmole) in water (5 ml). The solution was stirred at room temperature overnight, acidified with dilute hydrochloric acid and the tetrahydrofuran evaporated in vacuo. The resultant white precipitate was filtered, washed with water and dried in vacuo to give 160 mg (98%) of the title compound which was recrystallized from ethanol to give white crystals, mp 93°-5° C.

νmax (mull) 1730, 1700, 1610, 1575 (weak) 1515 cm$^{-1}$ δ(CDCl$_3$) 0.87 (3H, bt, J6 Hz, terminal CH$_3$), 1.27 (14H, m, (CH$_2$)$_7$), 2.13 (4H, t, m, J6 Hz, OCH$_2$CH$_2$+allylic CH$_2$), 2.56 (2H, t, J6 Hz, CH$_2$CO$_2$), 3.96, (2H, t, J6 Hz, OCH$_2$), 6.00 (1H, d.t, J$_d$ 15 Hz, J$_t$ 6 Hz, =CH$_2$—alkyl), 6.30 (1H, d, J15 Hz, Ar —CH=), 7.00 (4H, ABq, Δν41 Hz, J9 Hz, C$_6$H$_4$)

Mass spec. Observed mass 322. 2356, theoretical mass 332.2351 for C$_{21}$H$_{32}$O$_3$ Found C, 75.86; H, 9.75, C$_{21}$H$_{32}$O$_3$ requires C, 75.86; H, 9.70%.

Examples 79 to 92 (Table 6) were prepared in a similar manner to that described in Example 78.

TABLE 6

| Example No. | Stereochemistry of the double bond | | Position of side chain attachment | mp °C. | Recrystalisation solvent | Yield % | Formula | Analysis (calcd/Found) | |
|---|---|---|---|---|---|---|---|---|---|
| | n | m | | | | | | C | H |
| 79 | 10 | 1 | Z | 2 | 82 | Petroleum ether b.p. 60-80° | 44 | C$_{21}$H$_{32}$O$_3$ 0.5 H$_2$O | 73.85 74.91 | 9.74 9.34 |
| 80 | 5 | 3 | Z | 2 | oil | — | 91 | C$_{18}$H$_{26}$O$_3$ | 74.48 | 9.03 |

TABLE 6-continued $$\text{CH}_3(\text{CH}_2)_n\text{-(4-phenyl-3,2)-O(CH}_2)_m\text{CO}_2\text{H}$$

| Example No. | n | m | Stereochemistry of the double bond | Position of side chain attachment | mp °C. | Recrystalisation solvent | Yield % | Formula | Analysis (calcd/Found) C | H |
|---|---|---|---|---|---|---|---|---|---|---|
| 81 | 5 | 3 | E | 2 | 42 | Petroleum ether b.p. 40–60° | 94 | $C_{18}H_{26}O_3$ | 74.28 74.48 74.52 | 9.13 9.03 9.01 |
| 82 | 7 | 3 | Z | 2 | 41 | Petroleum ether b.p 40–60° | 77 | $C_{20}H_{30}O_3$ 0.5 $H_2O$ | 73.35 72.63 | 9.54 9.64 |
| 83 | 8 | 3 | E | 2 | ca 20 | — | 52 | $C_{21}H_{32}O_3$ 0.25 $H_2O$ | 74.84 74.44 | 9.72 9.61 |
| 84 | 10 | 3 | Z | 2 | 56 | hexane | 95 | $C_{23}H_{36}O_3$ | 76.62 76.69 | 10.06 9.76 |
| 85 | 10 | 3 | E | 2 | 51 | Petroleum ether b.p. 40–60° | 95 | $C_{23}H_{36}O_3$ | 76.62 76.77 | 10.06 10.23 |
| 86 | 10 | 4 | Z | 2 | 41 | Petroleum ether b.p.40–60° | 61 | $C_{24}H_{38}O_3$ | 76.96 77.01 | 10.23 10.19 |
| 87 | 10 | 4 | E | 2 | 53 | Petroleum ether b.p.40–60° | 61 | $C_{24}H_{38}O_3$ | 76.96 76.80 | 10.23 10.56 |
| 88 | 9 | 3 | Z | 3 | 45–47 | — | 93 | $C_{22}H_{34}O_3$ | 76.26 76.10 | 9.89 9.80 |
| 89 | 10 | 1 | Z | 4 | 79–80 | Petroleum ether b.p.40–60° | 49 | $C_{21}H_{32}O_3$ | 75.90 75.96 | 9.71 9.58 |
| 90 | 9 | 2 | Z | 4 | 80–82 | — | 35 | $C_{21}H_{32}O_3$ | 75.90 75.72 | 9.71 9.58 |
| 91 | 9 | 2 | E | 4 | 97–99 | — | 41 | $C_{21}H_{32}O_3$ | 75.90 75.87 | 9.71 9.86 |
| 92 | 8 | 3 | Z | 4 | 62–63 | Petroleum ether b.p.60–80° | 81 | $C_{21}H_{32}O_3$ | 75.90 75.77 | 9.71 9.99 |

EXAMPLE 93

Ethyl[4-2-(1,2-dibromooctyl)-phenoxy]-butanoate (E) Ethyl 4-[2-(1-octenyl)phenoxy]-butanoate, (1.40 g, 4.40M) was dissolved in carbon tetrachloride, (40 ml), and stirred at 10° C. Bromine, (0.23 ml, 4.40M), dissolved in carbon tetrachloride (10 ml) was added dropwise and the pale yellow solution stirred for 0.5 h, then partitioned between carbon tetrachloride and water. The organic phase was separated washed with dilute sodium thiosulphate, water and dried, (MgSO$_4$). Evaporation in vacuo gave the title compound in 95% yield, as a colourless oil, which was used without purification.

νmax, (film) 1490, 1590, 1600, 1738 cm$^{-1}$, δ, (CDCl$_3$), 0.89 (3H, distorted t, terminal CH$_3$), 1.27 (3H, t, J7 Hz, ester CH$_3$), 1.28 (10H, m, (CH$_2$)$_5$), 2.18 (2H, m, CHBrCH$_2$), 2.52 (2H, m, CH$_2$CO$_2$), 4.02 (2H, t, J, 6 Hz, OCH$_2$), 4.16 (2H, q, J7 Hz, ester CH$_2$), 4.40 (1H, m, CHBrCH$_2$), 5.67 (1H, d, J6 Hz, ArCHBr), 6.73 to 7.69 (4H, m, arom Hs).

EXAMPLE 94

Ethyl 4-[2-(1-octynyl)-phenoxy]-butanoate

A solution of ethyl 4-[2-(1,2-dibromooctyl)-phenoxy]butanoate, (2.01 g, 4.20 mmole), potassium t-butoxide, (1.33 g, 11.1 mmole) and $^{18}$crown$^6$(5 mg) in dry dimethylsulphoxide (25 ml) was stirred at ambient temperature for 4 h, then at 100° C. for 15 h. The reaction was evaporated in vacuo to a low volume, poured into saturated brine and acidified with dilute hydrochloric acid. The product was extracted with ethyl acetate (three times) and the combined organic phases washed with water (three times), and dried, (MgSO$_4$). Evaporation in vacuo yielded the crude product as a pale brown oil, which was purified by column chromatography using silica gel and eluting with dichloromethane/petroleum ether 60°-80° C., (1:1). The intermediate bromoalkane was collected first, followed by 0.380 g (29%) of the acetylene as a colourless oil.

νmax (film) 1442, 1465, 1490, 1570, 1595, 1738, 2225 (weak) cm$^{-1}$ δ(CDCl$_3$) 0.87 (3H, distorted t, terminal CH$_3$), 1.23 (3H, t, J7 Hz, ester CH$_3$), 1.34 (8H, m, (CH$_2$)$_4$), 2.16 (2H, m, CH$_2$CH$_2$CO$_2$), 2.43 (4H, m, CH$_2$CO$_2$, ≡—CH$_2$), 4.02 (2H, t, J7 Hz, OCH$_2$), 4.04 (2H, q, J7 Hz, ester CH$_2$), 7.05 (4H, m, arom Hs).

Mass Spec: Observed mass 316.2046, theoretical mass 316.2046 for $C_{20}H_{28}O_3$.

Found, C; 74.07, H; 8.67, $C_{20}H_{28}O_3$.0.5H$_2$O required C; 73.81; H; 8.98%.

EXAMPLE 95

4-[2-(1-Octynyl)-phenoxy]-butanoic acid

Ethyl 4-[2-(1-octynyl)-phenoxy]-butanoate, (250 mg, 0.79 mmole) was hydrolysed with 1 molar equivalent of lithium hydroxide using the same procedure as in example 9. Purification of the crude material by chromatography using silica gel, eluting with chloroform to chloroform/5% methanol afforded the title compound in 99% yield as a colourless oil.

νmax, film 1445, 1470 (weak), 1490, 1575, 1595, 1710, 2225 (weak) 3050 cm$^{-1}$. δ(CDCl$_3$) 0.85 (3H, distorted t, terminal CH$_3$), 1.42 (8H, m, (CH$_2$)$_4$), 2.13 (2H, m, CH$_2$CH$_2$CO$_2$), 2.42 (2H, t, J6 Hz, ≡—CH$_2$), 2.67 (2H, t, J6 Hz, CH$_2$CO$_2$), 4.00 (2H, t, J6 Hz, OCH$_2$), 6.90 (2H, m, arom Hs), 7.30 (2H, m, arom Hs), 8.37 (1H, bs, CO$_2$H, exchanged D$_2$O).

Mass Spec: Observed mass 288.1728, theoretical mass 288.1725 for C$_{18}$H$_{24}$O$_3$.

Found: C; 73.46, H; 8.41, C$_{18}$H$_{24}$O$_3$, 0.25H$_2$O required C; 73.82, H; 8.34%.

EXAMPLE 96

1-Methoxy-2-(1-octynyl)-benzene

2-Methoxyphenyl acetylene (9.00 g, 0.068M, Literature reference J. Villieras et al, Synthesis 459, 1975), was dissolved in dry, deaerated tetrahydrofuran/diethyl ether 1:1 (200 ml) and the solution stirred at −70° C. n-Butyl lithium 1.565M in hexane (43.5 ml, 0.068M) was added dropwise and the pale red mixture warmed to room temperature and stirred at that temperature for 15 min. The mixture was cooled to −70° C. and dry iodohexane (14.42 g, 0.068M) added dropwise. The white mixture was warmed to room temperature and stirred for 1 h, then refluxed for 4 h during which time a yellow solution formed. The reaction was cooled, poured into 1M sulphuric acid, (200 ml), and the product extracted with diethyl ether, (three times). The combined organic phases were washed with water, brine and dried, (MgSO$_4$). Evaporation in vacuo yielded the crude produce as a pale yellow oil. Purification with column chromatography using silica gel and eluting with dichloromethane/n-hexane (1:3) gave 12.58 g (86%) of the title compound as a colourless oil.

νmax, (film), 1435, 1463, 1490, 1577, 1600, 3225 (weak) cm$^{-1}$. δ(CDCl$_3$) 0.90 (3H, distorted t, terminal CH$_3$), 1.43 (8H, m, (CH$_2$)$_4$), 2.43 (2H, t, J6 Hz, ≡—CH$_2$), 3.87 (3H, s, OCH$_3$), 6.87 (2H, m, arom Hs), 7.28 (2H, m, arom Hs).

Using similar procedures to those outlined in the above examples were prepared the following compounds:

EXAMPLE 97

4-(1-Octynyl)cinnamic acid; m.p. (CH$_3$OH) 149°-153° C., Found; C, 79.27; H, 7.70; C$_{17}$H$_{20}$O$_2$ requires; C, 79.65; H, 7.86%

EXAMPLE 98

Methyl 2-[2-(1-tridecynyl)phenyl]acetate: oil, b.p. 190° C./0.05 mm (Kugelrohr distillation).

EXAMPLE 99

2-[2-(1-tridecynyl)phenyl]acetate acid: m.p. (CH$_3$OH—H$_2$O) 40°-42° C.

PHARMACOLOGICAL DATA

(1) Lipoxygenase Screen

Inhibition of lipoxygenase activity was measured at 25° C. in a buffered incubation system (0.2M sodium borate, pH 9.0) comprising 1000 I.U. soybean lipoxygenase, 0.017 mM arachidonic acid, and compound (0–0.050 mM, dissolved in absolute ethanol:0.9% w/v saline, 30:70 v/v) in a total volume of 2.5 ml. Enzyme and compound were preincubated together at 25° C. for 5 minutes prior to initiation of the lipoxygenase reaction by the addition of the arachidonic acid. Lipoxygenase activity was measured as the rate of the initial increase in absorbance at 235 nm due to the formation of peroxidised forms of arachidonic acid. Inhibitory activity was measured at at least three compound concentrations and the 50% inhibitory concentration determined from the plot of % inhibition versus compound concentration.

(2) Cyclo-oxygenase Screen

The inhibition of cyclo-oxygenase was measured in a buffered incubation (0.2M Tris-HCl, pH 8.0 containing 1 mM ethylene diaminetetraacetic acid) comprising 0.96 mg lyophilised bovine seminal vesicle microsomes, 5–15 μM arachidonic acid containing 0.2 μCi [1—$^{14}$C] arachidonic acid, 2 mM glutathione, 0.5M hydroquinone, 1 μM haemoglobin and compound (0–0.05 mM in 5 μl dimethylsulphoxide or absolute ethanol) in a total volume of 2.0 ml. Compounds were preincubated with the incubation constitutents for 5 min at 37° C. before the reaction was started by the addition of the arachidonic acid. The reaction was continued at 37° C. for 2 min, then stopped by placing the incubations on ice and the addition of 1.2 ml 0.2M citric acid. Unmetabolised substrate and prostaglandin products were extracted in ethyl acetate (2×4 ml), the combined extracts washed with 0.8 ml water, and separated by thin-layer chromatography (Kieselgel GF$_{254}$ plates in ethyl acetate:acetone:glacial acetate acid, 90:10:1, v/v). Recovery was 65–80%. The regions on the thin-layer chromatography plate that chromatographed with authentic arachidonic acid or prostaglandins E$_2$ and F$_2$α (R$_f$'s 0.70. 0.28 and 0.16 respectively) were scraped and the radioactivity in each determined by liquid scintillation counting with a correction for quenching being made by the external standard-channels ratio method. Inhibition of cyclo-oxygenase activity was calculated from the decrease in prostaglandin formation. Each compound concentration was tested in triplicate and the 50% inhibitory concentration, if determined, was calculated by linear regression from the inhibitory data at, at least three different compound concentrations.

The results in the two screens are as shown in the following table.

TABLE

| Example No. | Lipoxygenase Inhibition (IC$_{50}$, μM) | Cyclooxygenase Inhibition at 50 μM |
|---|---|---|
| 4 | 142 (128–160) | — |
| 9 | 272 (N—methylglucamine salt) | — |
| 12 | 85.7 (71–100) | 86.5 |
| 13 | — | 79.8 |
| 15 | 230 (141–277) | — |
| 24 | 30 (27–34) | 52 |
| 25 | 35.9 (32–41) | 25.6 |
| 26 | 52.3 (46–59) | 52 |
| 27 | 46.6 (35.1–57.4) | 70.5 |
| 29 | — | 66.5 |
| 30 | 23.2 | 26 |
| 31 | — | 91 |
| 40 | — | 67 |
| 41 | — | 40 |
| 42 | 20 (16.3–24.2) | 80 |
| 43 | 18.4 | 62.7 |
| 55 | 55.4 (50.1–60.4) | — |
| 60 | — | 92.4 |
| 61 | — | 78.9 |
| 62 | 4.2 (2.5–6.3) | 67 |
| 82 | — | 72 |
| 85 | — | 64 |
| 87 | — | 67 |
| 89 | 124 (88–263) | 51 |
| 90 | 75.3 (64–95) | — |

TABLE-continued

| Example No. | Lipoxygenase Inhibition (IC$_{50}$, μM) | Cyclooxygenase Inhibition at 50 μM |
|---|---|---|
| 92 | 42.8 (24.5–58.6) | — |

I claim:

1. A compound of formula (I):

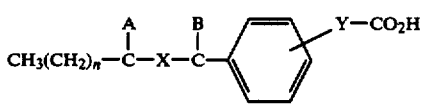

or a salt, ester or amide thereof,
in which
Y is a group —O(CH$_2$)$_m$—, —(CH$_2$)$_m$— or —CH=CH—
where
m is an integer of from 1 to 5
n is an integer of from
4 to 14
X represents a double or triple bond, and each of A and B represents hydrogen when X is a double bond, or both A and B are absent when X is a triple bond.

2. A compound according to claim 1, in which the substituents on the aromatic ring are in the 1,2 position.

3. A compound according to claim 1, in which n is an integer from 8 to 12.

4. A compound according to claim 1, in which m is 2, 3 or 4.

5. A compound according to claim 1 in which, when X is a double bond, the hydrocarbon chain containing X has the (Z) absolute configuration, or when Y is —CH=CH—, the —Y—CO$_2$H group has the (E) absolute configuration.

6. A compound according to claim 1, selected from
2-(1-tridecynyl)cinnamic acid,
4-[(Z)-1-undecenyl]cinnamic acid,
3-[2-(1-tridecynyl)phenyl]propanoic acid,
4-{2-[(Z)-1-tridecenyl]phenoxy}butanoic acid,
2-{2-[(Z)-1-tridecenyl]phenoxy}acetic acid, and
3-{2-[(Z)-1-tridecenyl]phenyl}propanoic acid.

7. A pharmaceutical composition comprising a compound according to claim 1, and a pharmaceutically acceptable carrier.

8. A composition according to claim 7, in unit dosage form.

9. A method for treating allergic diseases in human or non-human animals, which comprises administering to an animal in need thereof an effective, non toxic amount of a compound according to claim 1.

10. A process for preparing a compound according to claim 1, which comprises treating a compound of formula (II),

in which
Y is as defined with reference to formula (I),
V represents

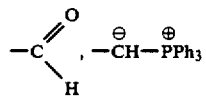

or halogen, and R is hydrogen or an ester forming group, with a compound of formula (III), CH$_3$(CH$_2$)$_n$—W     (III)

in which W is

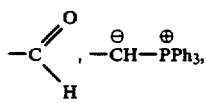

—CH=CH$_2$ or —C≡CH,
and, optionally thereafter reducing the carbon-carbon triple bond, when present in the resultant product, to a carbon-carbon double bond, and/or optionally coverting the resultant product, when R is an ester-forming group, to the corresponding acid or amide, with the provisos that
(i) when V is

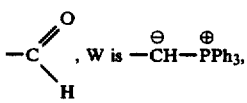

(ii) when V is

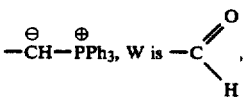

and
(iii) when V is halogen, W is —CH=CH$_2$ or —C≡CH.

11. A process for preparing a compound according to claim 1, which comprises treating a phenol of formula (IV),

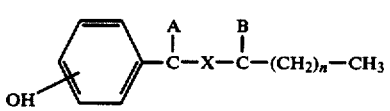

wherein n, X, A and B are defined in formula (I), with a compound of formula (V), Br(CH$_2$)$_m$CO$_2$R     (V)

wherein m is as defined in formula (I) and R is an ester forming group.

12. A process for preparing a compound according to claim 1, which comprises treating a compound of formula (VI),

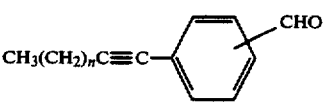

in which n is as defined in formula (I) with a compound of formula (VII), $$\overset{\oplus}{Ph_3P}-\overset{\ominus}{CH}-CO_2R \quad \text{(VII)}$$

in which R is an ester forming group.

13. A process for preparing a compound according to claim 1, which comprises brominating an ester of a compound of formula (I) in which Y is $-O-(CH_2)_m-$ or $-(CH_2)_m-$ and X is a double bond, and dehydrobrominating the resultant intermediate in which the $$-\overset{A}{\underset{|}{C}}-X-\overset{B}{\underset{|}{C}}-$$

moiety in formula (I) is replaced by

—CHBr—CHBr—.

* * * * *

UNITED STATES PATENT AND TRADEMARK OFFICE
CERTIFICATE OF CORRECTION

PATENT NO. : 4,713,486

DATED : December 15, 1987

INVENTOR(S) : Derek Richard Buckle

It is certified that error appears in the above-identified patent and that said Letters Patent is hereby corrected as shown below: Title page:

Related U.S. Application Data
Continuation of Serial No. 550,110,
Nov. 9, 1983, abandoned.

Signed and Sealed this

Twenty-eighth Day of June, 1988

*Attest:*

DONALD J. QUIGG

*Attesting Officer*   *Commissioner of Patents and Trademarks*